(12) United States Patent
Chelvam et al.

(10) Patent No.: US 11,518,786 B2
(45) Date of Patent: Dec. 6, 2022

(54) THIRD GENERATION TUBULYSIN ANALOGUES AND PROCESS OF PREPARATION THEREOF

(71) Applicant: Indian Institute of Technology Indore, Indore (IN)

(72) Inventors: Venkatesh Chelvam, Indore (IN); Amit Pandit, Indore (IN); Ramesh Reddy Baddipally, Narayanapet (IN); Kratika Yadav, Indore (IN); Biswarup Pathak, Indore (IN); Diptendu Roy, Indore (IN)

(73) Assignee: INDIAN INSTITUTE OF TECHNOLOGY INDORE, Indore (IN)

( * ) Notice: Subject to any disclaimer, the term of this patent is extended or adjusted under 35 U.S.C. 154(b) by 0 days.

(21) Appl. No.: 17/198,918

(22) Filed: Mar. 11, 2021

(65) Prior Publication Data
US 2022/0056079 A1 Feb. 24, 2022

(30) Foreign Application Priority Data
Aug. 21, 2020 (IN) .............................. 202021036140

(51) Int. Cl.
*C07K 9/00* (2006.01)
*A61P 35/00* (2006.01)

(52) U.S. Cl.
CPC .............. *C07K 9/003* (2013.01); *A61P 35/00* (2018.01)

(58) Field of Classification Search
CPC .................................. C07K 9/003; A61P 35/00
See application file for complete search history.

(56) References Cited

U.S. PATENT DOCUMENTS

2013/0217638 A1* 8/2013 Wessjohann ............ A61P 35/00
530/409

* cited by examiner

*Primary Examiner* — Jeanette M Lieb

(57) ABSTRACT

The present disclosure relates to a third generation tubulysin analogues and process of preparation thereof. The present disclosure also relates to a method of using these third generation tubulysin analogues for treatment of various diseases including cancer.

12 Claims, 15 Drawing Sheets

THIRD GENERATION TUBULYSIN ANALOGUES AND PROCESS OF PREPARATION THEREOF

FIELD OF INVENTION

The present disclosure relates to a third generation tubulysin analogues and process of preparation thereof. The present disclosure also relates to a method of using these third generation tubulysin analogues for treatment of various diseases including cancer. The present application is based on, and claims priority from an Indian Provisional Application Number 202021036140 filed on 21 Aug. 2020, the disclosure of which is hereby incorporated by reference herein.

BACKGROUND OF INVENTION

Cancer is known since ancient times and first reported by Egyptian and Greek physicians. Suffering from cancer has been observed in all age groups of global society, and the World Health Organization mark says one out of six deaths globally by cancer. Past 20 years, we have seen paradigm in the treatment of cancer. However, the current status of cancer treatment is very challenging because of the scarcity of FDA approved anticancer drugs, complex synthetic protocols, non-targeted drug delivery, development of drug resistance in cancers, and low bio-stability of the drug in the blood serum. The few FDA approved cancer therapies are very expensive which restrict its approachability to low economic patient group.

Currently available portfolio of anticancer drugs has its own drawbacks. These agents have shown side effects like hair and skin changes, anemia, bowel dysfunction, immune suppression, lung dysfunction, along with nausea, weight changes, and dietary issues. The nonspecific binding of anticancer drugs is responsible for these side effects. Targeting for cancer-specific cells can be achieved by conjugating the anticancer drugs with either monoclonal antibody or targeting ligand, which specifically binds with an antigen over-expressed over cancer cells. In cancer treatment, microRNAs (miRNAs) have received wide attention of researchers as they control the expression of the gene at the level of post-transcription. However, this approach has faced challenges because in vivo experimental models have reported low stability of RNA. This technique also encountered difficulties of targeted delivery along with the nonspecific binding of miRNAs. The miRNAs also affected by the first-pass metabolism.

Over the years, various researchers successfully targeted tubulysin derivatives to several cancer cell lines through this concept. Studies have suggested that cancer cells have at least two molecular pumps that expel out the cancer drug molecules. This leads to the condition of the multi-drug resistance of cancer cells against the treatment. This cellular response is accountable for the failure of a large number of chemotherapeutic agents available. In research, it has been identified that tubulysins do not get effluxed by these molecular pumps. So tubulysin derivatives have become potential drug candidates for the treatment of multidrug-resistant cancers.

The microtubule system has a very significant role in cellular events like maintenance of cellular morphology, control of intracellular transportation, regulation of mitotic spindle fiber formation, and cell division (Theg, D. E. Cytoplasmic microtubules in different animal cells. *J. Cell. Biol.* 1964, 23, 265-275). Significance of microtubule formation is further increased in the cancerous condition where frequent mitotic spindle formation is highly demanded for uncontrolled proliferation of cancer cells. Therefore, inhibition of microtubule formation emerges as a powerful tool to arrest or treat cancerous growth. Any event that disrupts microtubule assembly formation leads to mitotic arrest at metaphase of cell cycle and ultimately induces apoptosis of cells (Wilson, L. Action of drugs on microtubules. *Life Sci.* 1975, 17, 303-309). Microtubule dynamics is controlled by polymerization and de-polymerization of α- and β-tubulin proteins. Consequently, researchers have identified natural products or small molecules that block either polymerization or de-polymerization of tubulin protein and exhibit the cytotoxic effect intended to kill the cancer cells (Nogales, E.; Wolf, S. G.; Downing, K. H. Structure of the αβ tubulin dimer by electron crystallography. *Nature*, 1998, 391, 199-203). Recently, a family of natural products called tubulysins and their derivatives have emerged as an outstanding candidate for tubulin polymerization inhibitor. Höfle et al. (2000) first isolated tubulysin derivatives from two strains of Myxobacteria culture broths *Angiococcus disciformis* and *Archangium gephyra* (Sasse, F.; Steinmetz, H.; Heil, J.; Höfle, G.; Reichenbach, H. Tubulysins new cytostatic peptides from myxobacteria acting on microtubuli. Production, isolation, physico-chemical and biological properties. *J. Antibiot (Tokyo).* 2000, 53, 879-885). The natural tubulysin derivatives are termed as tubulysin A to I, U, V, and Z (FIG. 1). The structural composition of tubulysin family of natural products consists of four amino acid fragments. The first fragment is F-tubuphenylalanine or F-tubutyrosine, which is sequentially connected with F-tubuvaline, F-isoleucine, and N-methyl pipecolic acid. In few of the tubulysin derivatives, the amide linkage of tubuvaline and F-isoleucine is also functionalized. This family of natural products is the first generation of tubulysin antimitotic agents with several stereocenters.

Exhaustive literature search mentioned above concludes that the tubulysin derivatives are recognized as potent anticancer drugs with potency in nano to picomolar range to kill fast dividing cells. Isolation of natural tubulins is performed by the fermentation process. Conventionally used processes as such are extremely time consuming, expensive, laborious, often resulting in poor yields (0.5 mg to 4 mg per liter). Further, these methods also require multiple purification processes for isolation of a single derivative from the fermentation mixture, thereby making the whole process very cumbersome. The total synthesis of tubulysin derivatives by conventional processes is also challenging because fragments are complicated to synthesize, and epimerization occurs at various steps of synthesis. Moreover, these synthetic steps are inefficient and very intricate, with low yields Multiple research groups have put their efforts to synthesize either fragments or complete tubulysin natural products or their derivatives. Among them, Hofle., G et al in *Pure Appl. Chem.* 2003, 75, 167-178; Domling (*Tetrahedron Lett.* 2003, 44, 8947-8950), Wipf (*Org. Lett.* 2004, 22, 4057-4060) and Friestad (*Org. Lett.* 2004, 6, 3249-3252) have reported the total synthesis of L-tubuvaline and L-tubuphenylalanine/L-tubutyrosine fragments of tubulysin. The biosynthetic precursor tubulysin, named pretubulysin, was identified by Muller's group in year 2004 and his group later explored the inhibitor for its tubulin depolymerization activity (Sandmann, A.; *Chem. Biol.* 2004, II, 1071-1079). After two years in 2006, Ellman's research group developed a total synthesis (16-steps) of tubulysin D with 13% overall yield. As research on tubulysin family progressed, various biological pathways were identified for its cytotoxic property (Peltier, H. M.; et al. *J. Am. Chem. Soc.* 2006, 128, 16018-16019). For the first time, Agarwal's research group in 2006 explored the antiangiogenic property of the tubulysin A.

Meanwhile, new synthetic derivatives of natural tubulysin were also explored to identify its structure activity correlation for cytotoxic activity. In year 2007, the Ellman's group reported ten analogues of tubulysin D by modifying different fragments. They suggested that the modifications in fragments are well tolerated. In the same year, Wipf's group reported a total asymmetric synthesis of N14-desacetoxytubulysin H in 20-steps with only 2.1% overall yield. This molecule later named as tubulysin M suggest that N,O-acetal fragment is not crucial for inhibitory activity. Further in 2008, Fecik's research group also developed new and simplified derivatives of tubulysin by modifying N-methyl pipecolinic acid and L-tubuphenylalanine residues. However, cytotoxic activities of these derivatives were found to be in the micromolar range not suitable for preclinical trials. In the same year, Ellman optimized the asymmetric total synthesis of tubulysin derivative with linear steps and 40% overall yield.

As tubulysin was established as potent cytotoxic agent, research groups put the efforts to target it by conjugating with targeting ligand and also developed various drug delivery systems. In 2008, Endocyte, Inc. USA successfully conjugated potent tubulysin derivative with folic acid to target the folate receptor positive cancers and thereby developed the first targeted therapy of tubulysin derivative. They have claimed the folate targeted antiproliferative activity of water-soluble folic acid conjugated tubulysin derivative by in vitro and in vivo models (Leamon, C. P.; *Cancer Res.* 2008, 68, 9839-9844). Later in year 2009, Schluep's group covalently attached the tubulysin A to linear, β-cyclodextrin based polymer through disulfide linker and evaluated its activity by in vitro and in vivo models. These prodrug constructs improved the therapeutic index of tubulysin derivatives but failed to show further clinical efficacy (Schluep, T.; *Clin. Cancer Res.* 2009, 15, 181-189). Further in year 2011, Ellman conjugated tubulysin analogue with dendrimer by acyl hydrazone linkage and developed a polymeric drug delivery system for tubulysin derivatives. This improved the stability, lowered the toxicity, and enhanced the water solubility for in vivo evaluation (Floyd W. C.; et al, *Chem. Med. Chem.* 2011, 6, 49-53).

Wessjohann's group, in year 2011, reported the second generation of tubulysin derivative named "Tubugis" by multicomponent reactions. In the new derivatives N,O-acetal ester moiety, which is sensitive for acidic and basic condition, is replaced by more stable retro-amide. The GI50 value for tubugis derivative is in the high picomolar range which is quite interesting (Pando, O.; et. al, *J. Am. Chem. Soc.* 2011, 133, 7692-7695).

In the year 2014, Dongen's groups developed antibody-drug conjugate using tubulysin derivative as drug. In this research, they have radiolabelled two tubulysin derivatives and conjugated with the anti-HER2 monoclonal antibody (mAh), named trastuzumab, and successfully analysed its potential for targeting tumour and consequently antitumor effects in nude mice (Cohen, R.; *Cancer Res.* 2014, 74, 5700-5710). In the same year, Steinmetz's group identified a new binding site which is different from *vinca* domain and consequently inhibits the longitudinal interactions of tubulin protein (Protaa, A. E.; et al, *PNAS.* 2014, 111, 13817-13821).

In the year 2015, Low's group developed another targeted therapy by conjugating the tubulysin B with cholecystokinin 2 receptor targeting ligand. Cholecystokinin 2 receptor is overexpressed in many lung, pancreas, liver, and GI tract cancers. They selectively delivered tubulysin B to Cholecystokinin 2 receptor-positive tumors (Wayua, C.; et al, *Mol. Pharmaceutics.* 2015, 12, 2477-2483).

Further, more synthetic derivatives based on second generation tubulysin, tubugi, were developed and evaluated by Kazmaier's group (2015) by modifying the acylal side chain. They reported that nonpolar side chains like allyl or propargyl groups are more tolerated, while polar side chains like amide are less tolerated for cytotoxic activity (Hoffmann, J.; et al *Org. Biomol. Chem.* 2015, 13, 6010-6020). In the same year, Ryu and Lee developed new derivatives of tubulysin where tubuvaline moiety was cyclized. They reported that the cyclization induced the structural rigidity, which drastically reduced the tubulin polymerization efficacy. They reported that the cyclization induced structural rigidity drastically reduced tubulin polymerization efficacy. They reported that the cyclization induced the structural rigidity, which drastically reduced the tubulin polymerization efficacy (Park Y.; et al *Bioorgan. Med. Chem.* 2015, 23, 6827-6843).

Toader's group (2016) modified the N-methyl pipecolic acid and tubuphenylalanine moieties with various different fragments and explained the relationship between the basicity of N-terminus of tubulysin derivative and its cytotoxicity (Toader, D.; et al *J. Med Chem.* 2016, 59, 10781-10787). In the same year, Nicolaou's group also synthesised several tubulysin derivatives by modifying all four fragments and evaluated its cytotoxic activity. They have summarized all the results as a structure-activity relationship and claimed that N-methyl-D-pipecolinic acid is essential for activity, whereas isoleucine domain can be modified by other lipophilic groups. Also, L-tubuvaline and L-tubuphenylalanine are much affected by modification for their cytotoxicity activity (Nicolaou, K. C.; et al *J. Am. Chem. Soc.* 2016, 138, 1698-1708).

A similar analysis was also performed by Wipf (2016), and he tabulated some of the tolerated and non-tolerated fragments for N-methyl-D-pipecolinic acid, tubuvaline, and tubuphenylalanine (Colombo, R.; et al, *J. Org. Chem.* 2016, 81, 10302-10320). Further, in the same year, Zhang's group provided the pharmacophoric details of tubulysin derivatives. They analyzed the crystal structure of microtubule with tubulysin M as a co-crystallised inhibitor. They claimed that tubulysin predominantly bound with the β subunit of tubulin and exhibited the cytotoxicity effect (Wang, Y.; Benz, F. W.; Wu, Y.; Wang, Q.; Chen, Y.; Chen, X.; Li, H.; Zhang, Y.; Zhang, R.; Yang, J. Structural insights into the pharmacophore of *vinca* domain inhibitors of microtubules, *Mol. Pharmacol.* 2016, 89, 233-242). Further in 2016, tubulysin based antibody-drug conjugate was optimised by Turney's (Turney, L. N.; et al, *ACS Med. Chem. Lett.* 2016, 7, 977-982) along with Leverett and Sukuru's group of Pfizer inc. USA (Leverett, C. A.; Sukuru, et al, *ACS Med. Chem. Lett.* 2016, 7, 999-1004). They designed tubulysin derivatives which might be the best candidates for antibody drug conjugation and having less liability for metabolism and with improved cytotoxicity.

In year 2017, Low's group developed tubulysin based therapy by selectively targeting cancer cells which overexpress carbonic anhydrase IX. They reported that the conjugate shown cytotoxicity in the range of mid-nanomolar and also good tumor selectivity in the in vivo models (Lv, P. C.; Roy, J.; Putt, K. S.; Low, P. S. Evaluation of Nonpeptidic Ligand Conjugates for the treatment of hypoxic and carbonic anhydrase IX-expressing cancers. *Mol. Cancer. Ther.* 2017, 16, 453-460). In the same year, Low's group developed one more therapy targeting neurokinin 1 receptor-expressing cancers like melanomas, gliomas neuroblastomas, pancreatic ductal carcinomas, retinoblastomas, invasive breast cancers and colon carcinomas. In this therapeutic construct, targeting ligand is connected to tubulysin B hydrazide through a hydrophilic linker. The $IC_{50}$ of developed tubulysin based therapeutic agent was found to be 10 nM (Kanduluru, A. K.; Low, P. S. Development of a ligand-targeted therapeutic agent for neurokinin-1 receptor expressing cancers. *Mol. Pharmaceutics.* 2017, 14, 3859-3865). In same year, Pillow's group reported an approach to develop stable and bio-reversible antibody-tubulysin conjugate without loss of activity (Staben, et al, *ACS Med Chem. Lett.* 2017, 8, 1037-1041). Also, Parker's group from AstraZeneca reported the solid phase peptide synthesis-based development of antibody-tubulysin conjugate payload. They optimized the synthetic strategy and achieved overall yield from 0.01% to 2.4%.

In 2018, Endocyte performed preclinical and clinical (Phase I and II) evaluation of this targeted therapy. They reported that the treatment showed substantial anti-cancer activity against the animal model of FR-positive tumors, even in drug-resistant cases. In the same year, Nicolaou's group designed and synthesized various tubulysin-based derivatives, and some derivatives shown excellent cytotoxic potency in the range of pico-molar. In 2018, our research group also reported new strategy for the synthesis of L-tubuphenylalanine and epi-tubuphenylalanine fragments of tubulysin. In 2019, Endocyte targeted prostate cancer biomarker named prostate-specific membrane antigen (PSMA), by conjugating tubulysin B with a targeting ligand. Through in vitro and in vivo evaluation, they claimed that PSMA positive cancer could be treated by tubulysin based PSMA targeting conjugates, but the human clinical trials have a glitch due to possible instability of the tubulysin family of natural products in the serum.

In 2019, a new strategy for large scale synthesis of deacetoxytubuvaline fragment of pretubulysin and its highly lipophilic methyl-substituted thiazole and oxazole analogues for incorporation into pretubulysins was reported (Reddy, R. B.; Dudhe, P.; Chelvam, V. Synthesis of the deacetoxytubuvaline fragment of pretubulysin and its lipophilic analogues for enhanced permeability in cancer cell lines, *Synlett.* 2019, 30, 77-81). The strategy is mentioned in FIG. 2.

In an unpublished work, (Reddy, R. B.; Chelvam V) has also developed a convenient strategy for the practical and scalable synthesis of L-tubuvaline fragment of L-tubulysin natural products by asymmetric dihydroxylation of N-tosylhomoallylamine from commercially available L-valine. The synthetic strategy developed in our laboratory is depicted in FIG. 3. Though the strategy is simple and reduced the total number of linear steps, the preparation of thiazole in large quantities posed a big problem in industrial manufacturing sectors. Therefore, we resorted to a disruptive modification step to change the molecular structure of tubulysin totally to obtain third generation of tubulysin family of natural products. This can be performed by replacing sensitive, pharmacologically active moiety F-tubvaline fragment containing a chiral centre and thiazole moiety with another thiazole moiety without any chiral center, as shown in FIG. 3.

Thus, it is desired to address the above-mentioned disadvantages or other shortcomings or at least provide a useful alternative. The present disclosure herein solves the above problems by third-generation tubulysin derivatives, fragments of which are easy to synthesize by traditional solution-phase synthesis, and all the fragments are coupled by solid-phase peptide synthesis.

OBJECT OF INVENTION

The principal object of the embodiments herein is to provide for third-generation tubulysin derivatives effective against the multidrug resistance cancers.

Another objective of the present invention is to provide a synthetically feasible, convenient, cost-effective, simple, process of preparation of third-generation tubulysin derivatives.

Yet another objective of the present invention is to provide for third-generation tubulysin conjugate therapy for cancer-specific targeting, including multi-drug resistant cancer.

Yet another objective of the present invention is to provide for a bio-stable solution for cancer treatment, which can be targeted by conjugating with the ligand.

SUMMARY OF INVENTION

Accordingly, embodiments herein disclose third-generation tubulysin derivatives effective against the multidrug resistance cancers. Embodiments also provide a synthetically feasible, convenient, cost-effective, simple, process of preparation of third-generation tubulysin derivatives. For this purpose, a library of novel tubulysin derivatives have been designed, synthesized, and biologically evaluated as new anticancer agents. The designing of new inhibitors has been done by detailed in silico study, including quantitative structure-activity relationship (QSAR) and molecular docking study. Through this study, a comprehensive SAR for tubulysin derivative for its anticancer property is conducted. Also, critical fragments of tubulysin derivatives have been identified, which are very important for antiproliferative activity. Consequently, novel tubulysin derivatives have been designed on the basis of proposed SAR. Further, those derivatives which have displayed better results in the theoretical study have been synthesized by a combination of solution-phase and solid-phase peptide synthesis. Synthesized derivatives have been evaluated for their anti-proliferative property by in vitro cytotoxicity assay against various types of cancer cell lines like lung cancer (A549), breast cancer (MCF-7), cervical cancer (HeLa) and skin cancer (A431). Initial cytotoxicity assay data was encouraging with $IC_{50}$ in the sub-nanomolar range for incubation period of 24 and 48 h. The cytotoxicity of third generation tubulysin derivatives were compared with standard anticancer drug doxorubicin and the newly synthesized tubulysin derivatives were found to be 100-250 fold more potent than doxorubicin.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This method is illustrated in the accompanying drawings, throughout which like reference letters indicate corresponding parts in the various figures. The embodiments herein will be better understood from the following description with reference to the drawings, in which:

DETAILED DESCRIPTION OF INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

Figure 1:
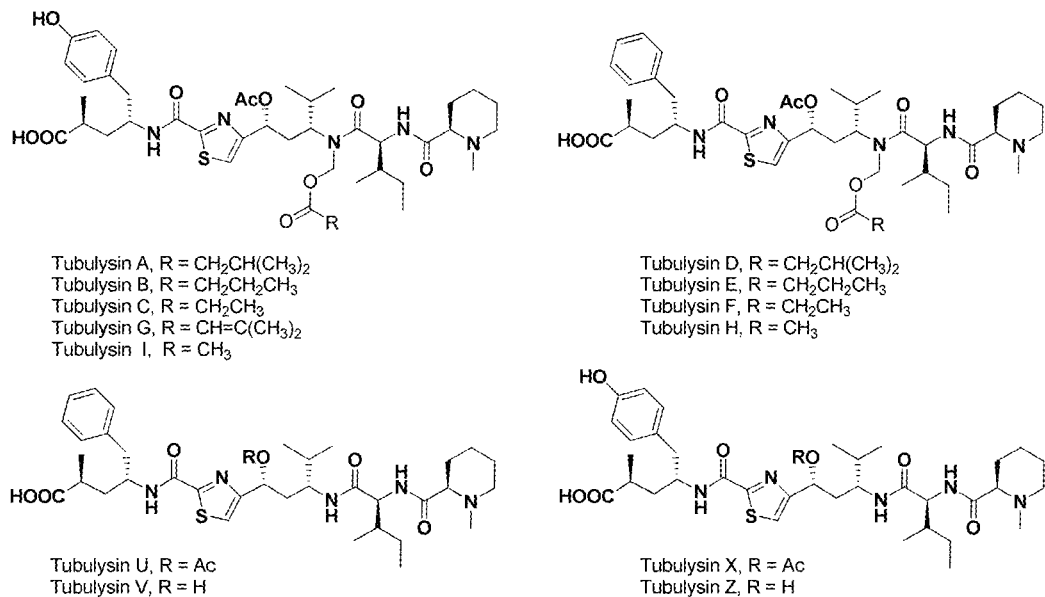
FIG. 1 illustrates structure of natural tubulysin derivatives, according to an embodiment as disclosed herein.
Figure 2:
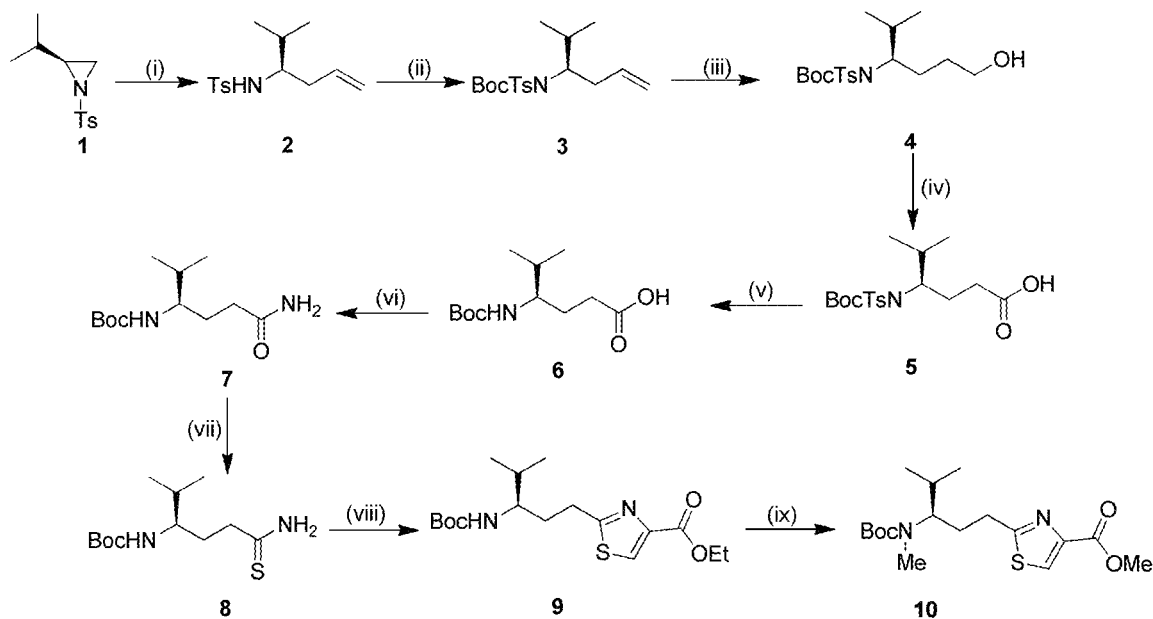
FIG. 2 illustrates a scheme for synthesis of deacetoxytubuvaline (existing literature), according to an embodiment as disclosed herein.
Figure 3:
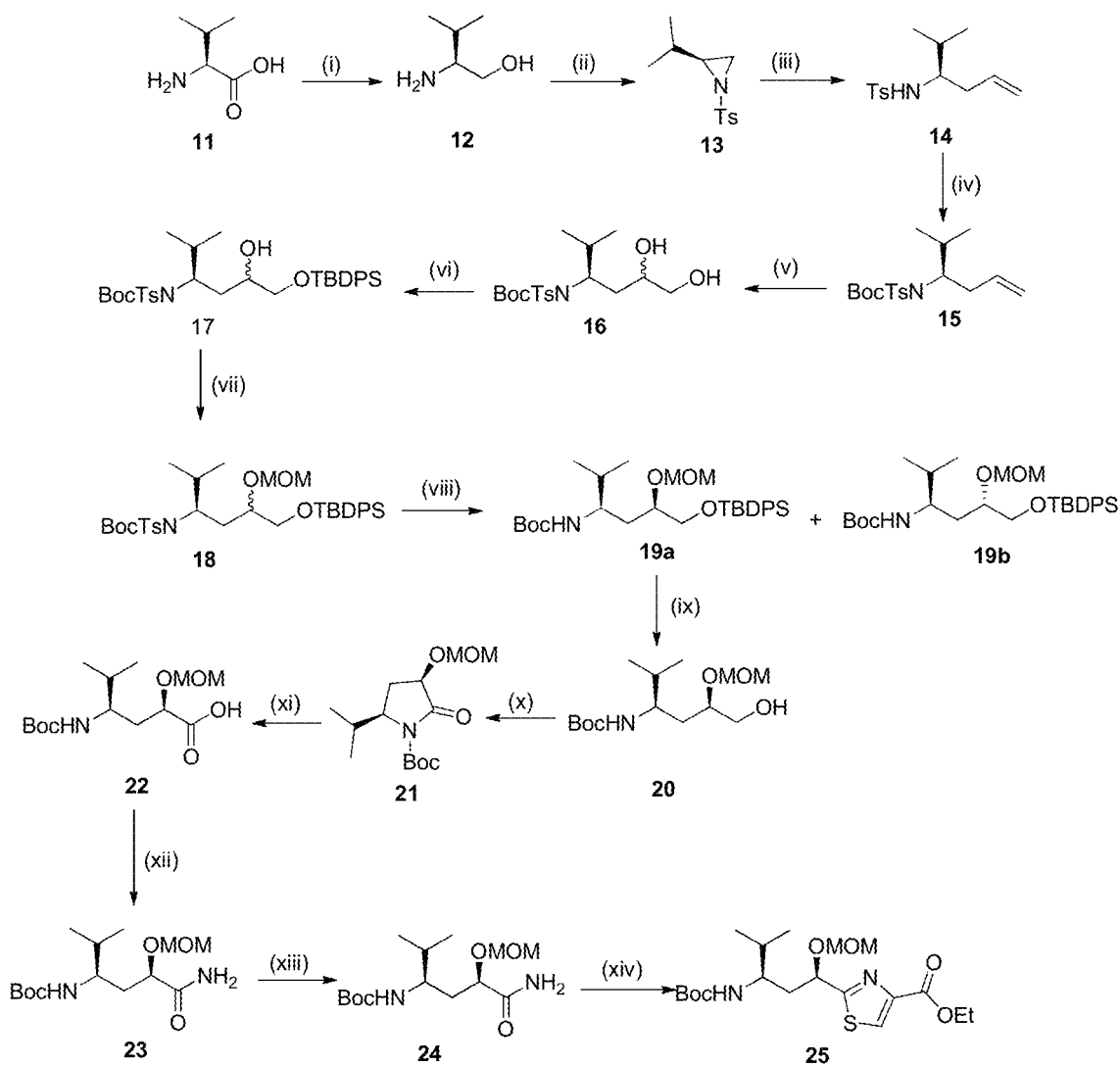
FIG. 3 illustrates a scheme for synthesis of N-Boc γ-substituted α-hydroxy γ-amino acid, according to an embodiment as disclosed herein.
Figure 4:
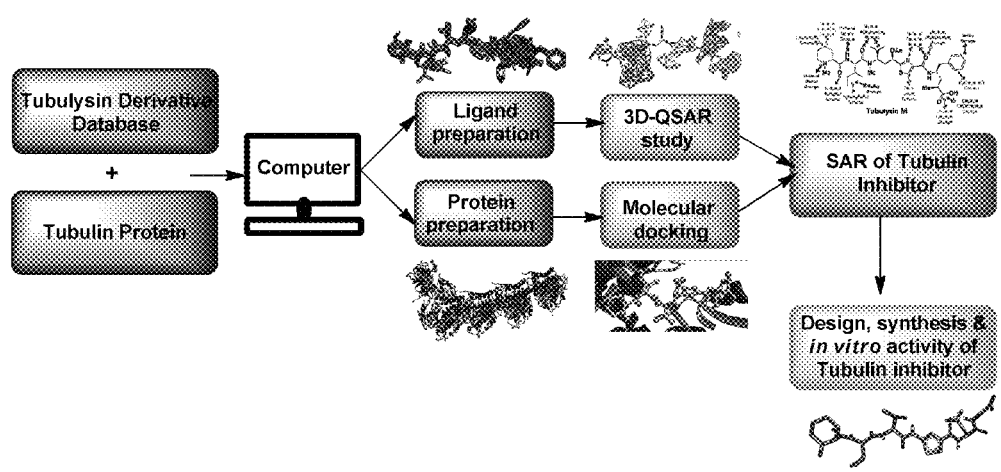
FIG. 4 illustrates schematic representation of new drug molecules (tubulysin derivatives of the present invention), according to an embodiment as disclosed herein.

Accordingly, embodiments describe a third-generation tubulysin derivatives effective against the multidrug resistance cancers. Embodiments also provide a synthetically feasible, convenient, cost-effective, simple, process of preparation of third-generation tubulysin derivatives. For this purpose, the following steps were carried out (FIG. 4):

a) three-dimensional quantitative structure-activity relationship (3D-QSAR) based in silico study of tubulysin derivatives for anticancer activity—structural analysis of potent tubulysin derivatives with the help of CoMFA and CoMSIA in silico modules of software and identifying critical fragments of tubulysin derivatives, which are responsible for anticancer activity;

b) molecular docking based in silico study of tubulysin derivative for discovering anticancer activity—computational analysis of the tubulysin binding site on tubulin protein and identifying the crucial interactions between tubulysin derivative and amino acid residues of tubulin protein by molecular docking study;

c) development of structure-activity relationship (SAR) for tubulysin derivatives on the basis of in silico research—This was done by summarizing the results of the QSAR and molecular docking studies in the form of a comprehensive structure-activity relationship (SAR) of tubulysin derivative as an anticancer agent; design of the novel, third-generation tubulysin derivatives by the application of the outcomes of SAR study;

d) density Functional Theory (DFT) and QM/MM calculations results of new tubulysin derivatives with protein tubulin;

e) rational design and synthesis of third-generation tubulysin derivatives—solution phase synthesis of fragments of novel tubulysin derivatives and solid phase synthesis of final third generation tubulysin derivatives;

f) In vitro studies against human cancer cell lines; and
g) synthesis and biological evaluation of third generation tubulysin derivatives—evaluation of the anticancer activity of third-generation tubulysin derivatives by in vitro and in vivo assay against various human cancer models.

Three-dimensional quantitative structure-activity relationship (3D-QSAR) based in silico study of tubulysin derivatives for anticancer activity: Natural tubulysins were first isolated from Myxobacteria strains in the year 2000. Since then, tubulysins have gained much attention of researchers for its high cytotoxic activity against cancer cells. Various research groups have synthesized natural and unnatural tubulysin derivatives. But to date, no exhaustive in silico study and accompanying synthesis and biological activity has been reported. In this invention, novel third-generation tubulysin derivatives through extensive theoretical study have been designed, synthesised, and evaluated by biological evaluation.

In the first study, we have analyzed a dataset of reported unnatural tubulysin derivatives and correlated the three-dimensional structural features of inhibitors with several cytotoxicity activities. A complete theoretical study was performed on molecular modeling software, SYBYL X 2.1.1. The development of 3D-QSAR models was performed by the application of two methods, i.e., comparative molecular field analysis (CoMFA) and comparative molecular similarity index analysis (CoMSIA). The structural dataset was divided into test and training data sets. The model was developed by the training set and validated by the test set. In the CoMFA method, electrostatic and steric field properties were analyzed for the structure-activity relationship study. In the CoMSIA method, five field interaction parameters such as steric (S), electrostatic (E), hydrophobic (H), hydrogen bond donor (D) and acceptor (A) abilities were analyzed, and the QSAR models were generated. The partial least square (PLS) method was applied to determine the statistical correlation between CoMFA and CoMSIA field parameters for predicted and experimental IC50 of tubulysin derivatives. The most significant QSAR model, which gives the best correlation of structural features of tubulysin derivatives with its biological activity, is selected on the basis of most optimum statistical parameters. For CoMFA, the best model was found with statistical features such as cross-validated correlation coefficient ($q2=0.59$), non-cross-validated correlation coefficient ($r2=0.93$), fitness test ($F=92.22$), standard error of estimation ($SEE=0.32$) and predicted square correlation coefficient ($r2$ $pred=0.87$). The field contributions in this model were 65% of steric and 35% of electrostatic interactions, which suggested the dominance of steric type of interactions for cytotoxic activity of tubulysin derivatives. For CoMSIA, the best model was found with optimum q2 (0.58), high r2 (0.94), low SE (0.35), significant ONC (7), F values (73.11) and r2 pred (0.93). The combination of field parameters for the selected model was found to be with S, E, H, and A with field contribution of 15%, 29%, 36%, and 20%, respectively. Here, the hydrophobic field contribution was found to be the dominating parameter for the cytotoxicity of tubulysin derivatives.

Figure 5:
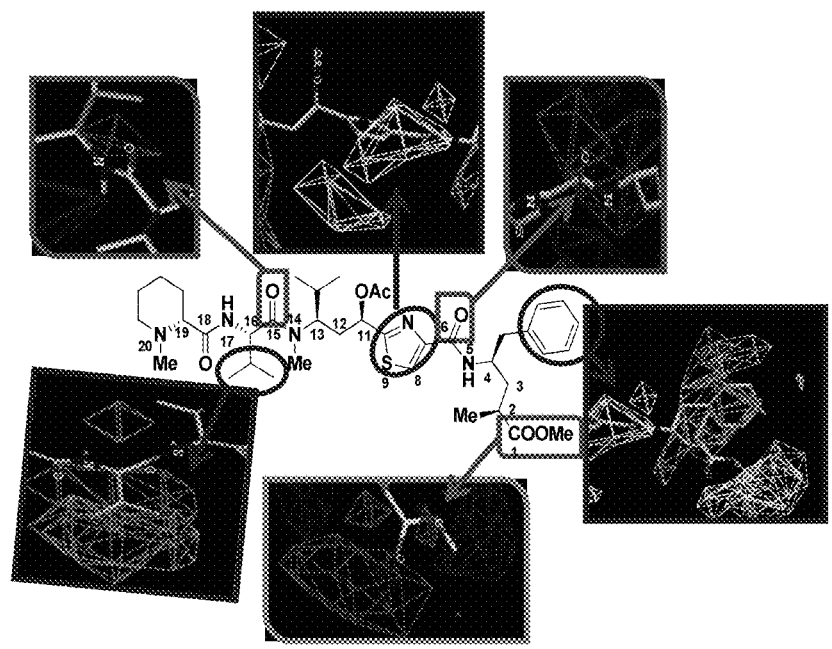
FIG. 5 illustrates contour maps for tubulysin derivatives from QSAR model, according to an embodiment as disclosed herein.

As shown in FIG. 5, green colored steric contour plot predicts the structural requirements of tubulin inhibitors where bulky group substitutions may amplify the biological activity whereas modifications at site denoted by yellow colored polyhedron contour show decrease in tubulin protein inhibition activity. In the best QSAR model, sterically favored region was expected to favor tubulin inhibition activity at C-16 position which is unequivocally established from the reported experimental. Similar steric influence on activity was predicted at C-4 position because of the presence of benzylic group. However, absence of steric crowding is mandatory at C-8 as per QSAR steric contour map. Further, the electrostatic field effects on inhibitory activity are denoted by blue and red color contour plots (FIG. 5). Blue contour plot signifies the fragment, where the presence of electron donating substituents will increase the biological activity. Similarly, the fragments representing red color contour plot suggests required modifications of the inhibitor with electron withdrawing functional groups that would increase the inhibitory activity. As per QSAR model analysis, red color contour map spreads over functional groups present at C-1, C-6 and C-15 positions. This analysis reveals that electron withdrawing substitutions at these carbon chain positions could be a dominating factor for better tubulin inhibitory activity. Accordingly, electronegative carbonyl oxygen atom at C-1, C-6 and C-15 positions of all the data set inhibitors contribute substantially for anti-tubulin activity. The QSAR study also suggested that replacement of C-11 and C-12 alkyl fragments by amide functionality would not hamper the inhibitory activity of molecule. This modification would also simplify the synthetic strategy and new inhibitors could be prepared by the solid phase peptide synthesis methodology.

Figure 6:
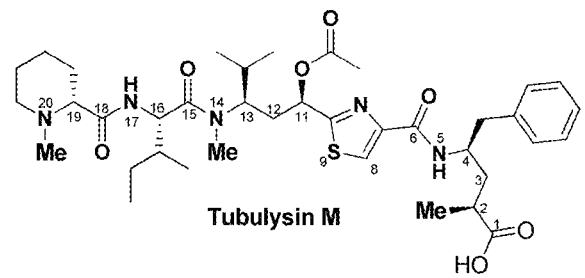
FIG. 6 illustrates structure of tubulysin M, according to an embodiment as disclosed herein.
Figure 7:
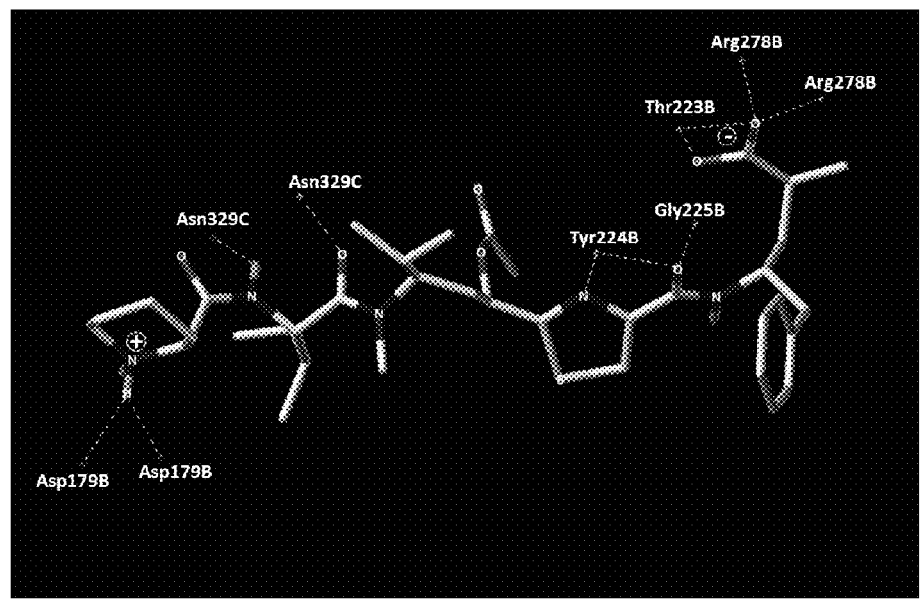
FIG. 7 illustrates post docking hydrogen bonding interactions of Tubulysin M in the active site of tubulin protein (PDB ID 4ZOL), according to an embodiment as disclosed herein.

Molecular docking based in silico study of tubulysin derivative for anticancer activity: Interaction with protein is a necessary requirement for the drug's biological action. Theoretically, this interaction can be analyzed by molecular docking study. Post QSAR study, the molecular docking study was performed by retrieving tubulin protein (PDB code:4ZOL) from the protein data bank, which was co-crystallized with one of the potent tubulysin, Tubulysin M (FIG. 6). Complete docking studies were performed by the Surflex-Dock method using Sybyl X 2.1.1. Following the protein preparation module, the site of the co-crystallized inhibitor is designated as protomol, and docking was performed at that site. Binding interactions of tubulin protein and inhibitors were analyzed by the MOLCAD program of SYBYL. The interpretation of the result was made by appropriate color coding or lipophilic, hydrogen bond donor, and acceptor field interactions. High, moderate, and low lipophilic areas of interaction of tubulysin in the active cavity of tubulin protein are denoted by brown, green, and blue colors, respectively. Hydrogen bond donor and acceptor areas on tubulin active cavity are indicated by red and blue colors, respectively, while the grey color represents the non-polar area. The docking protocol was validated by re-docking of co-crystalized ligand tubulysin M. Post-docking molecular orientation of tubulysin M was then compared with its co-crystallized orientation which is reported in protein data bank with PDB code 4ZOL. The post-docking H-bonding interactions between tubulysin M and active site amino acid residues were depicted in FIG. 7 and also compared with reported interactions in Table 1.

TABLE 1

Comparative hydrogen bonding interactions of Tubulysin M with the amino acid residues at the tubulin active site

| Amino protein chain | Acids with the Tubulysin M | The structural moiety of Native pose | H-bond length Docked pose |
|---|---|---|---|
| Tyr224B | Thiazole ring nitrogen | 3.16 | 2.21 |
|  | C-6 Amide carbonyl oxygen | 3.04 | 2.33 |
| Gly225B | C-6 Amide carbonyl oxygen | 2.86 | 1.87 |
| Arg278B | C-1 Carboxylate oxygen | 2.85 | 1.95 |
|  | C-1 Carboxylate oxygen | — | 2.14 |
| Thr223B | C-1 Carboxylate oxygen | 2.83 | 2.08 |
|  | C-1 Carboxylate oxygen | — | 2.21 |
| Asn329C | N-17 Amide nitrogen | 2.85 | 1.83 |
|  | C-15 Amide carbonyl oxygen | 3.24 | 2.36 |
| Asp179B | N-20 Piperidinium nitrogen | — | 1.83 |
|  | N-20 Piperidinium nitrogen | — | 2.45 |

Tubulin protein is a heterodimer consisting of two subunits: α and β-tubulin chains designated as C and B-chains, respectively. In the literature, tubulysin M forms seven H-bonding interactions with five amino acid residues of B and C chains of tubulin proteins. Tyr224B amino acid residue of chain B forms two H-bonding interactions with the C-6 amide carbonyl oxygen and nitrogen atom present in the thiazole ring of the inhibitor, whereas Gly225B interacts only with the C-6 amide carbonyl oxygen functionality. Both Arg278B and Thr223B amino acid residues of B chain forms H-bonding interactions simultaneously with the C-1 carboxylate oxygen of tubulysin M. In the C chain of 4ZOL, Asn329C residue forms two H-bonds: one with C-15 amide carbonyl oxygen and another with the N-17 amide group of tubulysin M. These seven H-bonding interactions are present in the native pose of the inhibitor with the tubulin protein and are very crucial for the efficient binding of the inhibitor at the tubulin active site. In the case of the docked pose of the inhibitor in addition to the seven H-bonding interactions present in the native pose, four extra H-bonding interactions are observed (Table 1). Arg278B and Thr223B amino acid residues form the first two additional H-bonding interactions with the C-1 carboxylate group of the inhibitor, whereas Asp179B amino acid residue forms the other two new H-bonding interactions with the protonated nitrogen atom of the piperidine ring that are totally absent in the native pose. Finally, it can be inferred that the present protocol for molecular docking of tubulin inhibitors is accurate and reliable to analyze the interactions of the newly designed inhibitors.

Figure 8:
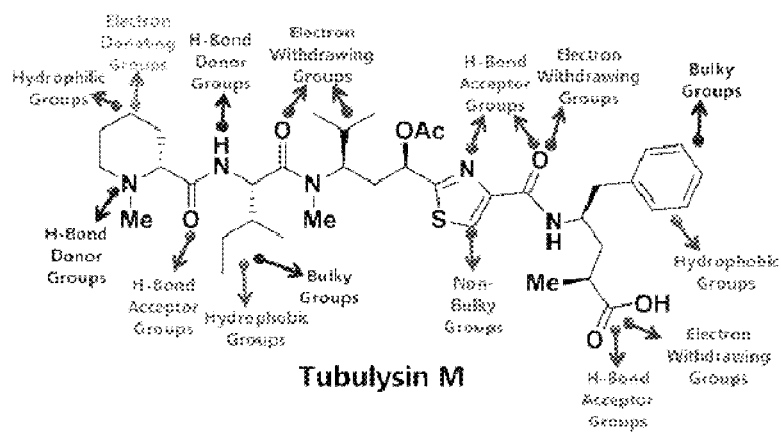
FIG. 8 illustrates structure-activity relationships (SARs) road map of tubulysin for designing potent tubulin inhibitors, according to an embodiment as disclosed herein.

Development of structure-activity relationship (SAR) for tubulysin derivatives on the basis of in silico study: The 3D-QSAR and molecular docking study was performed to identify the structural features of tubulysin derivatives, which are responsible for the anti-tubulin activity, and the results of both the methods were found to be coherent. The results of both in silico studies were analyzed and summarized in the form of a structure-activity relationship (SAR). The SAR study results are depicted in FIG. 8, which provided valuable guidance for designing of novel potent tubulysin derivatives. Various regions of tubulysin M that are susceptible to different substitution patterns with electron donating-withdrawing, bulky-non-bulky, hydrogen bond donor-acceptor, and hydrophobic-hydrophilic groups will provide a road map to prepare highly desirable tubulin inhibitors.

Density Functional Theory (DFT) and QM/MM calculations of new tubulysin derivatives with protein tubulin: Density functional theory (DFT) and quantum mechanics/molecular mechanics (QM/MM) based calculations are being carried out to identify the structural features of tubulysin derivatives, which are responsible for the anti-tubulin activity, and the results of both the methods were found to be promising. The results of both the studies show that various regions of tubulysin M that are susceptible to electronic nature of the different substitution patterns which is very promising to provide a road map to prepare highly desirable tubulin inhibitors.

Rational designing and synthesis of third generation tubulysin derivative: After exhaustive SAR study, third generation tubulin inhibitors were designed, as presented in FIG. 9. The inhibitors so designed are compounds of Formula I and Formula II

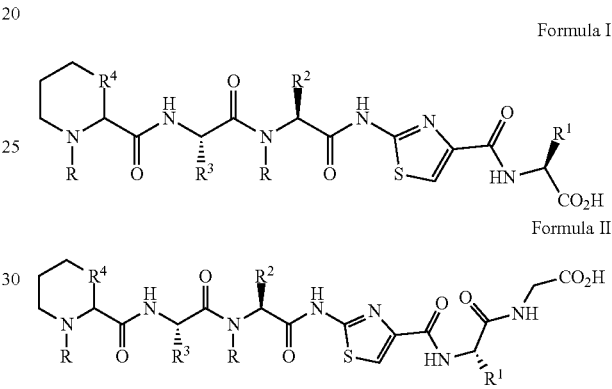

and its stereo isomers thereof, wherein R is a methyl group;

$R_1$ is one of $CH_2CONHTrt$, $(CH_2)_2COO^tBu$, and $CH_2COOH$ for compounds of Formula I; and $R_1$ is one of $CH_2COO^tBu$, $(CH_2)_2COO^tBu$, $CH_2Ph$, and $CH_2$—$C_6H_4$-p-$O^tBu$ for compounds of Formula II;

$R_2$ is $CH(CH_3)_2$, $R_3$ is $CH(CH_3)CH_2CH_3$, and $R_4$ is —$(CH_2)_4$ or

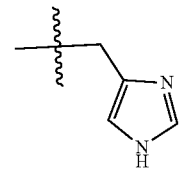 [SMILES: *Cc1c[nH]cn1]

Figure 9:
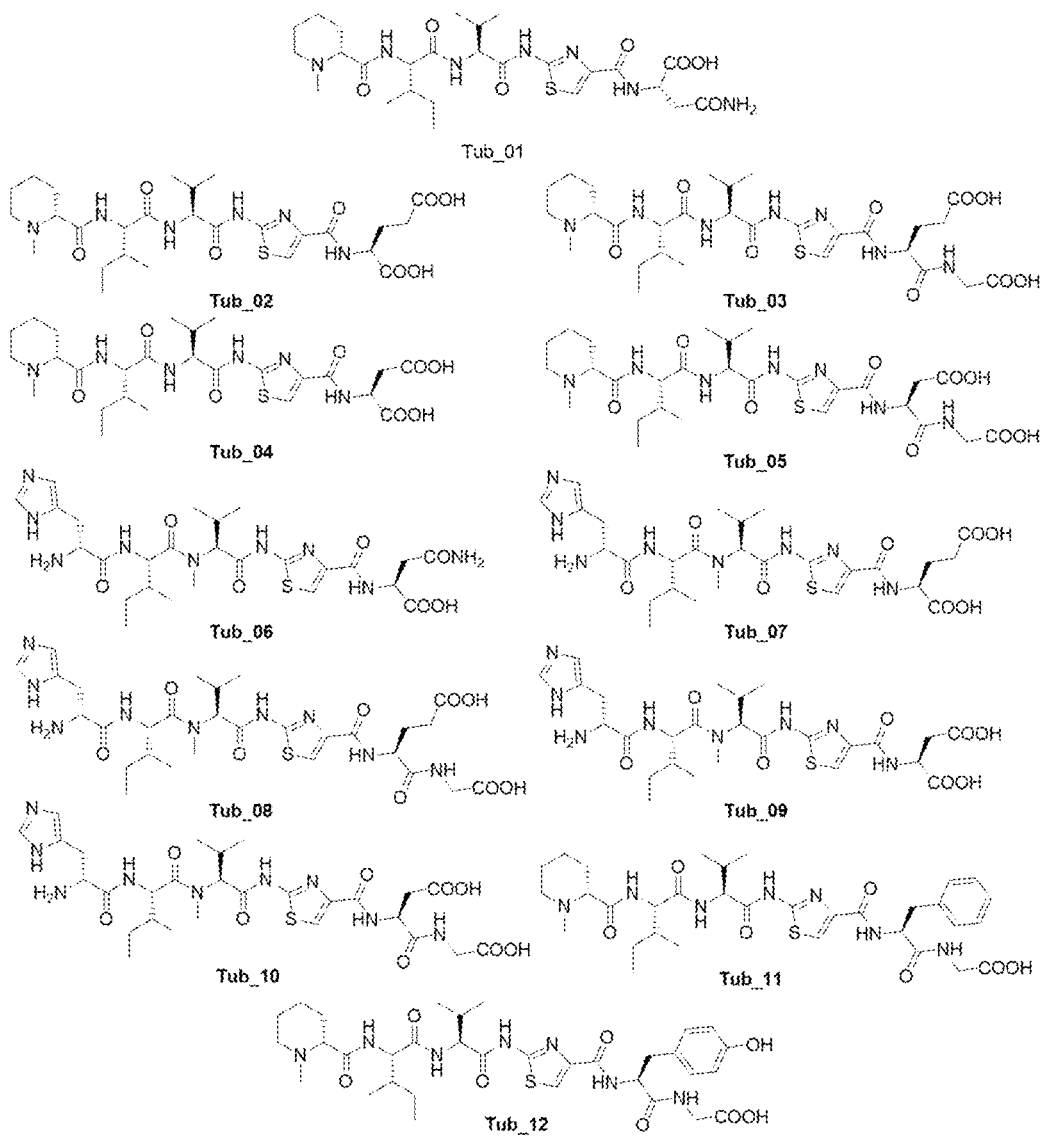
FIG. 9 illustrates third generation tubulysin derivatives of the present invention, according to an embodiment as disclosed herein.
Figure 10:
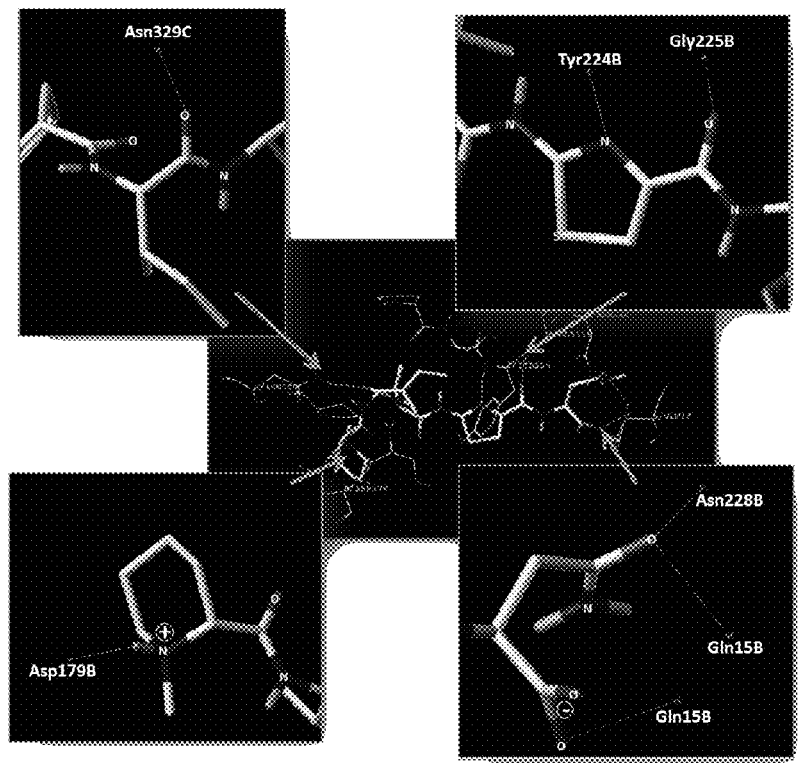
FIG. 10 illustrates post docking hydrogen bonding interactions of Tub_01 in the active site of tubulin protein (PDB ID 4ZOL), according to an embodiment as disclosed herein.

As can be observed from FIG. 9, Tub_01, the structure of the first inhibitor, was theoretically analyzed by above mentioned molecular docking protocol. The hydrogen bonding interactions of Tub_01 at active site of tubulin protein are depicted in FIG. 10. In molecular docking study of Tub_01 at tubulin active site, similar amino acid residues interacted with inhibitor through hydrogen bonds as reported with co-crystallized Tubulysin M. N-methyl pipecolic acid moiety interacted with Asp179 amino acid residue of B chain of tubulin protein. Asn329 of C chain, Tyr 224 and Gly225 of B chain also interacted in a similar way. Due to structural modification of Tub_01, two new hydrogen bonding interactions were found with Gln15 and Asn228 residues of B chain of tubulin protein. Molecular docking study of Tub_01 suggested that the designed inhibitor interacted with tubulin protein in a similar way as compared to co-crystallized inhibitor tubulysin M. These results motivated us to synthesize the designed inhibitor and validate the theoretical studies by experimental in vitro cytotoxic analysis.

Figure 11:
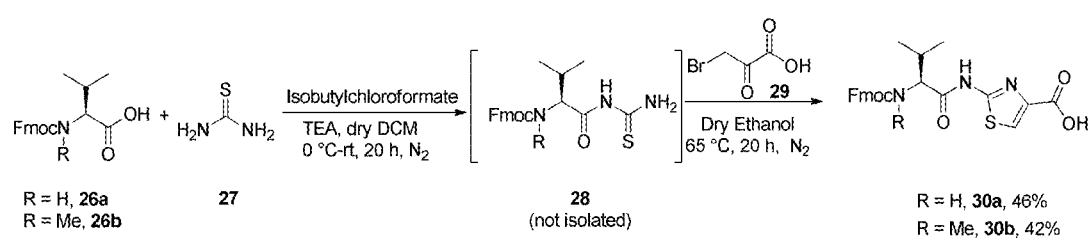
FIG. 11 illustrates a schematic representation of synthesis of Fmoc-NH-valine-thiazole (30a) and Fmoc-NMe-valine-thiazole (30b) moiety as tubulysin fragment, according to an embodiment as disclosed herein.

Chemical Synthetic Strategy for the Preparation of Third-Generation Tubulysin Derivatives Part A: Chemical Synthesis of Fmoc-NH-Valine-Thiazole and Fmoc-NMe-Valine-Thiazole Fragments (30a and 30b): The chemical synthesis of important fragments of tubulysin derivatives, Fmoc-NH-valine-thiazole (30a) and Fmoc-NMe-valine-thiazole (30b) begin with amide coupling reaction of Fmoc-NH-protected valine (26a) or Fmoc-NMe-protected valine (26b) and thiourea (27) in presence of carboxylic acid activating agent isobutyl chloroformate and base triethylamine under inert environment. In the next step, reaction intermediate 28 without isolation was treated with bromopyruvic acid (29) under inert atmosphere to yield desired Fmoc-NH-valine-thiazole (30a) and Fmoc-NMe-valine-thiazole (30b) in 46% and 42% yields respectively (FIG. 11).

Figure 12:
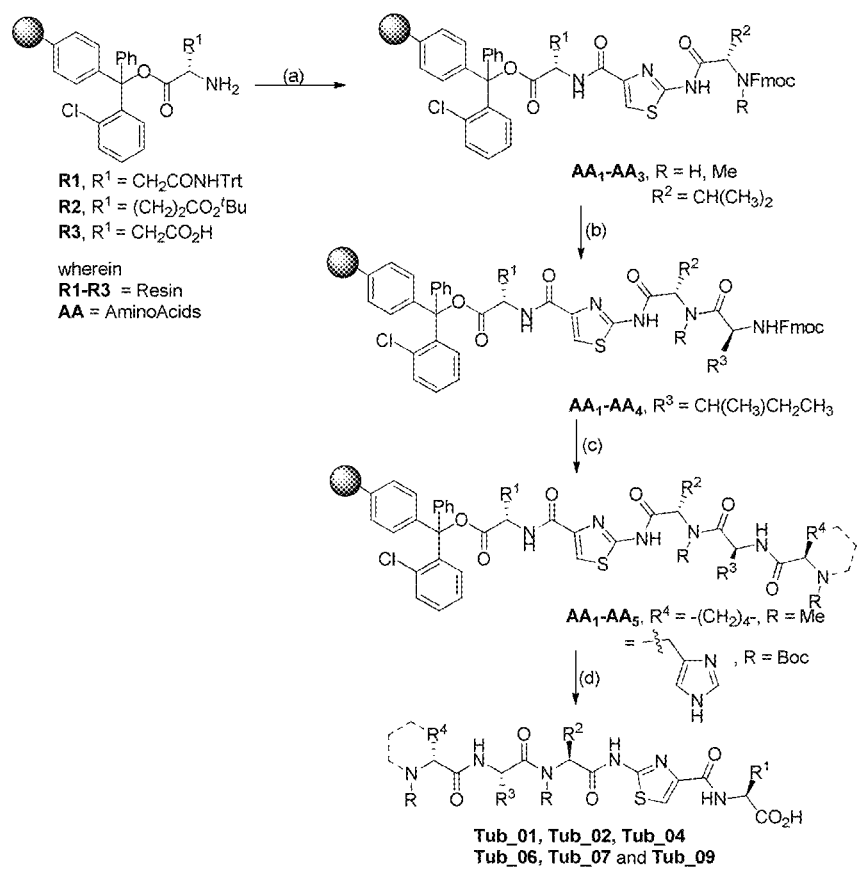
FIG. 12 illustrates a general schematic representation of solid phase synthetic strategy for the preparation of tubulysin derivatives Tub_01, Tub_02, Tub_04, Tub_06, Tub_07 and Tub_09, according to an embodiment as disclosed herein.

Part B: General Procedure for the Solid-phase peptide synthesis of third-generation tubulysin derivatives for Tub_01, Tub_02, Tub_04, Tub_06, Tub_07 and Tub_09, as illustrated in FIG. 12: In the first step, H-L-Asn(Trt)-2CT resin ($R_1$) or H-L-Glu(O$^t$Bu)-2-ClTrt resin (R2) or H-L-Asp (O$^t$Bu)-2-ClTn resin (R3) (0.14 mmol) was swelled with dichloromethane (5 mL) by bubbling nitrogen for 30 minutes and then drain the solvent. Later the resin was further swelled with DMF (5 mL) thrice for 15 minutes each. Fmoc-NH-Val-thiazole-OH, 30a or Fmoc-NMe-valine-thiazole 30b (0.35 mmol), PyBOP (0.182 g, 0.35 mmol) and DIPEA (0.24 mL, 1.4 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads didn't show dark blue color, which suggest that the free amine groups of resin beads were coupled with 30a or 30b. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment 30a or 30b. The resin beads were washed with DMF (3 mL×3), and isopropanol (3 mL×3), and the Kaiser test was performed. In the Kaiser test the beads turned to dark red in color indicating formation of free amino functionality in the tripeptide $AA_1$-$AA_3$. TO ensure amide coupling, the coupling reaction was extended for another 6 hours and again verified with the Kaiser test. After the confirmation of amide coupling, Fmoc-Ile-OH was next coupled with tripeptide $AA_1$-$AA_3$ without Fmoc functionality to give tetrapeptide $AA_1$-$AA_4$. After the deprotection of NHFmoc functionality using 20% piperidine in DMF, finally N-methylpipecolic acid or Boc-His-OH was attached to the growing peptide chain to obtain pentapeptide $AA_1$-$AA_5$. A mixture of 9.5 mL trifluoroacetic acid (TFA), 0.25 mL triisopropylsilane (TIPS), and 0.25 mL $H_2O$ was prepared in a 15 mL centrifuge tube, and 5 mL of this cocktail solution was added to the resin beads, and nitrogen gas was bubbled through the solution for 30 minutes. The cocktail with cleaved tubulysin derivatives in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved tubulysin derivatives was transferred to a 15 mL centrifuge tube, fitted with a septum, and concentrated under reduced pressure to obtain a viscous liquid. Ice cold ether (5 mL) was added to the concentrated, viscous mixture to precipitate tubulysin derivatives Tub_01, Tub_02, Tub_04, Tub_06, Tub_07, Tub_09 as white solids, and the solids were washed thrice with ice-cold ether (5 mL×3). The crude solids were dissolved in distilled DCM and kept for recrystallization. The white crystals were separated, washed and the molecular weight determined by HRMS (+ESI).

Figure 13:
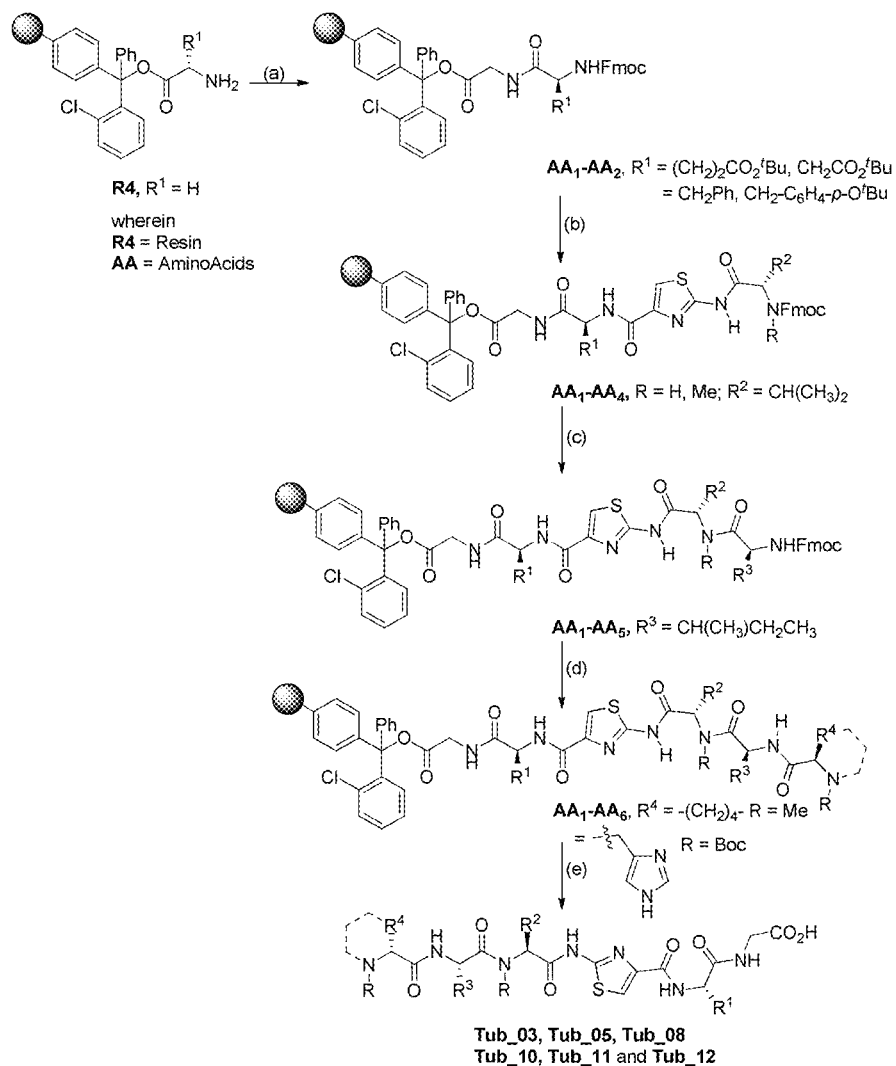
FIG. 13 illustrates a general schematic representation of solid phase synthetic strategy for the preparation of tubulysin derivatives Tub_03, Tub_05, Tub_08, Tub_10, Tub_11 and Tub_12, according to an embodiment as disclosed herein.

FIG. 13 illustrates a general schematic representation of solid phase synthetic strategy for the preparation of tubulysin derivatives Tub_03, Tub_05, Tub_08, Tub_10, Tub_11 and Tub_12: Part B: In the first step, H-Gly-2-Chlorotrityl resin R4 (0.1 g, 0.04 mmol) was swelled with dichloromethane (5 mL) by bubbling nitrogen for 30 minutes and then drain the solvent. Later the resin was further swelled with DMF (5 mL×3) 15 minutes each. Fmoc-Glu(γ-O$^t$Bu)—OH or Fmoc-Asp(O$^t$Bu)—OH or Fmoc-Phe-OH or Fmoc-Tyr ($^t$Bu)—OH (0.11 mmol), PyBOP (0.057 g, 0.11 mmol) and DIPEA (0.07 mL, 0.44 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads were colorless, which suggest that the free amine groups of resin beads were coupled with resin R4. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment of resin R4. The resin beads were washed with DMF (3 mL×3), and isopropanol (3 mL×3), and the Kaiser test was performed. The beads showed dark blue color, which suggest the formation of free amino functionality in the dipeptide $A_1$-$A_2$. Fmoc-Val-thiazole-OH, 30a or Fmoc-NMe-valine-thiazole 30b (0.11 mmol), PyBOP (0.057 g, 0.11 mmol) and DIPEA (0.07 mL, 0.44 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads were colorless, which suggest that the free amine groups of resin beads were coupled with Fmoc-Val-thiazole-OH. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment Fmoc-Val-thiazole-OH. The resin beads were washed with DMF (3 mL×3), and isopropanol (3 mL×3), and the Kaiser test was performed. In the Kaiser test, the beads turned to dark red in color indicating formation of free amino functionality in the tetrapeptide $A_1$-$A_4$. After the confirmation of free amine formation, Fmoc-Ile-OH (0.042 g, 0.11 mmol) was next coupled with tetrapeptide $A_4$-$A_4$ without Fmoc functionality to give pentapeptide $A_1$-$A_5$. After the deprotection of NHFmoc functionality using 20% piperidine in DMF, finally N-methylpipecolic acid or Boc-His-OH (0.11 mmol) was coupled to the growing peptide chain to obtain hexapeptide $A_1$-$A_6$. A mixture of 9.5 mL trifluoroacetic acid (TFA), 0.25 mL triisopropylsilane (TIPS), and 0.25 mL $H_2O$ was prepared in a 15 mL centrifuge tube, and 5 mL of this cocktail solution was added to the resin beads, and nitrogen gas was bubbled through the solution for 30 minutes. The cocktail with cleaved tubulysin derivatives in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved tubulysin derivatives was transferred to a 15 mL centrifuge tube, fitted with a septum, and concentrated under reduced pressure to obtain a viscous liquid. Ice cold ether (5 mL) was added to the concentrated, viscous mixture to precipitate tubulysin derivatives Tub_03, Tub_05, Tub_08, Tub_10, Tub_11 and Tub_12 as white solids, and the solids were washed thrice with ice-cold ether (5 mL×3). The tubulysin derivatives were purified by HPLC and the molecular weight is determined by HRMS (+ESI).

Figure 14:
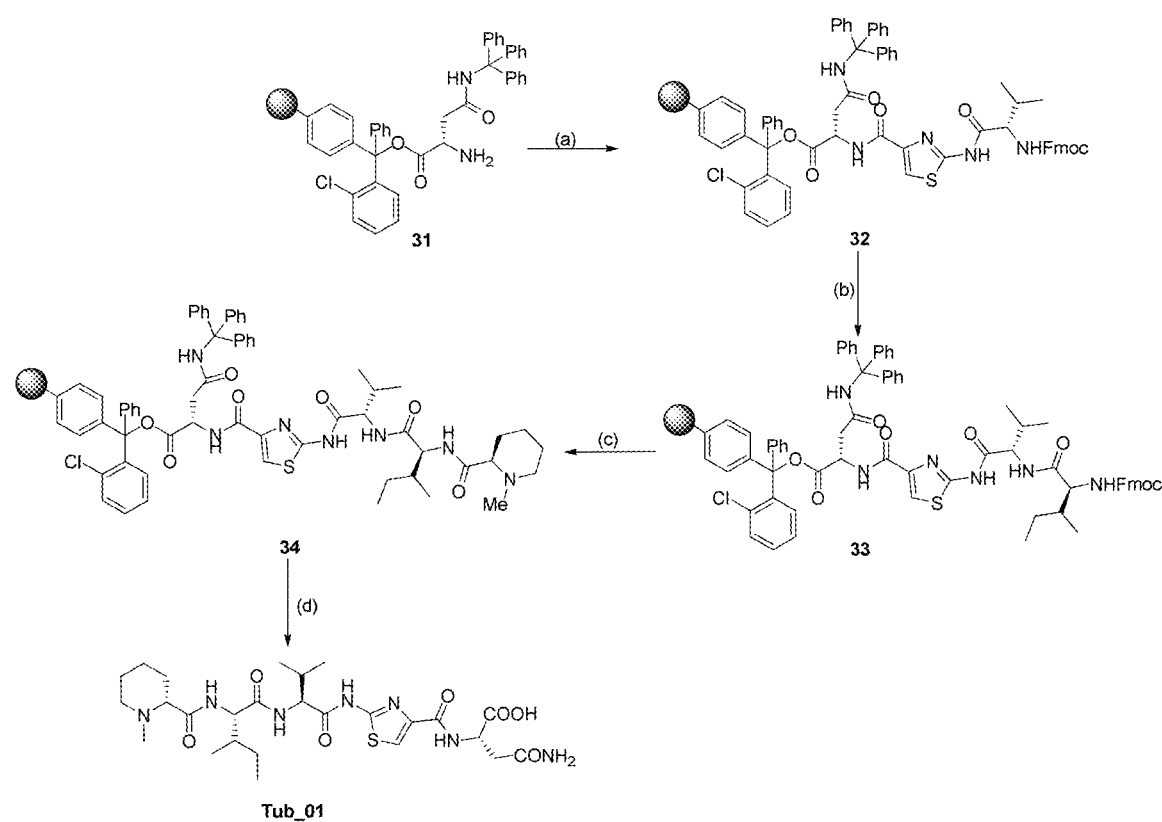
FIG. 14 illustrates a schematic representation of solid phase synthetic strategy for preparation of tubulysin derivative Tub_01, according to an embodiment as disclosed herein.

Chemical synthetic strategy for the preparation of third-generation tubulysin derivative Tub_01 (FIG. 14): In the first step, H-L-Asn(Trt)-2CT resin 31 (0.250 g, 0.14 mmol) was swelled with dichloromethane (5 mL) by bubbling nitrogen for 30 minutes and then drain the solvent. Later the resin was further swelled with DMF (5 mL) thrice for 15 minutes each. Fmoc-NH-Val-thiazole-OH, 30a (0.163 g, 0.35 mmol), PyBOP (0.182 g, 0.35 mmol) and DIPEA (0.24 mL, 1.4 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads didn't show dark blue color, which suggest that the free amine groups of resin beads were coupled with 30a. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment 30a. The resin beads were washed with DMF (3 mL×3), and isopropanol (3 mL×3), and the Kaiser test was performed. In the Kaiser test the beads turned to dark red in color indicating formation of free amino functionality in the tripeptide 32. To ensure amide coupling, the coupling reaction was extended for another 6 hours and again verified with the Kaiser test. After the confirmation of amide coupling, Fmoc-Ile-OH was next coupled with tripeptide 32 without Fmoc functionality to give tetrapeptide 33. After the deprotection of NHFmoc functionality using 20% piperidine in DMF, finally N-methylpipecolic acid was attached to the growing peptide chain to obtain pentapeptide 34. A mixture of 9.5 mL trifluoroacetic acid (TFA), 0.25 mL triisopropylsilane (TIPS), and 0.25 mL H$_2$O was prepared in a 15 mL centrifuge tube, and 5 mL of this cocktail solution was added to the resin beads, and nitrogen gas was bubbled through the solution for 30 minutes. The cocktail with cleaved Tub_01 in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved Tub_01 was transferred to a 15 mL centrifuge tube, fitted with a septum, and concentrated under reduced pressure to obtain a viscous liquid. Ice cold ether (5 mL) was added to the concentrated, viscous mixture to precipitate Tub_01 as a white solid, and the solid was washed thrice with ice-cold ether (5 mL×3). The solid crude (20% yield) was dissolved in distilled DCM and kept for recrystallization. The white crystals were separated and washed. The molecular weight is determined by HRMS (+ESI) calcd for [M+H]$^+$ (C$_{26}$H$_{41}$N$_7$O$_7$S)$^+$: 596.2861 found 596.2868.

Figure 15:
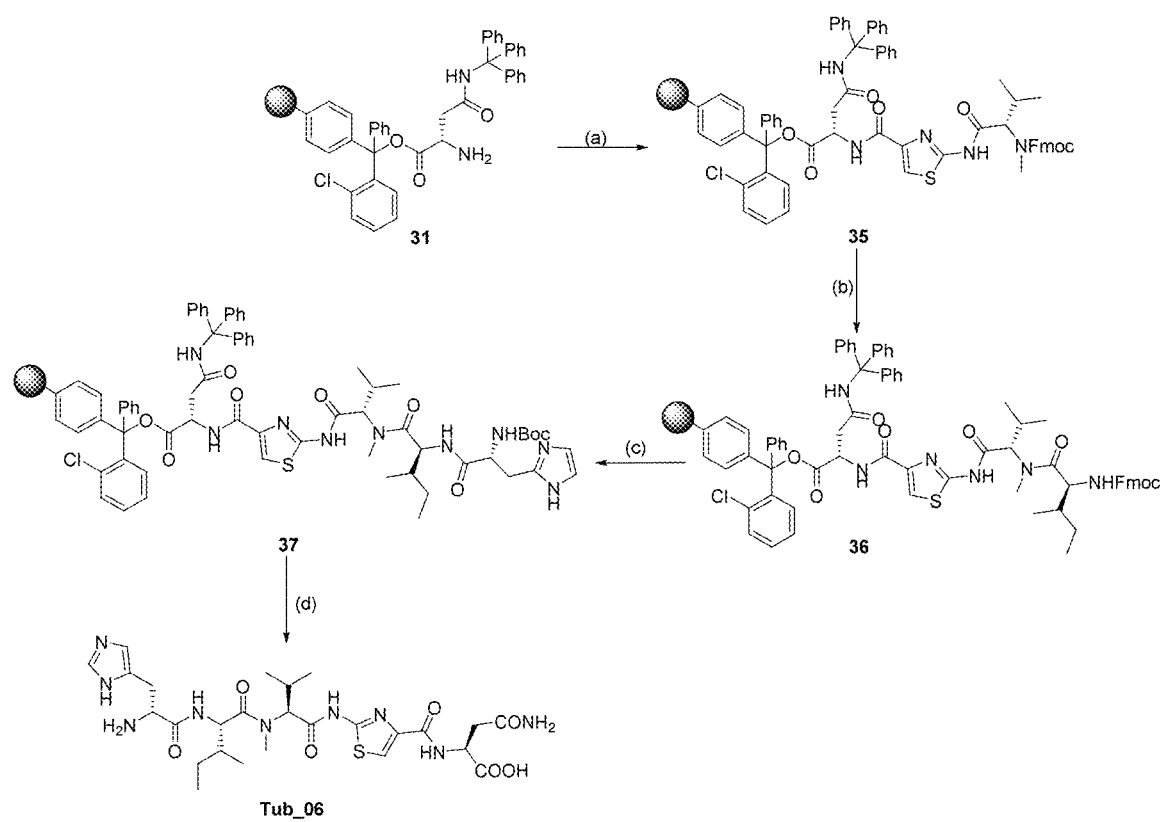
FIG. 15 illustrates a schematic representation of solid phase synthetic strategy for preparation of tubulysin derivative Tub_06, according to an embodiment as disclosed herein.

Preparation of Tub_06 (FIG. 15): In the first step, H-L-Asn(Trt)-2CT resin 31 (0.100 g, 0.056 mmol) was swelled with dichloromethane (5 mL) by bubbling nitrogen for 30 minutes and then drain the solvent. Later, the resin was further swelled with DMF (5 mL) thrice for 15 minutes each. Fmoc-NMe-valine-thiazole-OH 30b (0.067 g, 0.14 mmol), PyBOP (0.072 g, 0.14 mmol) and DIPEA (0.1 mL, 0.56 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads didn't show dark blue color, which suggest that the free amine groups of resin beads were coupled with 30b. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment 35. The resin beads were washed with DMF (3 mL×3), and isopropanol (3 mL×3), and the Kaiser test was performed. In the Kaiser test the beads turned to dark red in color indicating formation of free amino functionality in the tripeptide 35. After the confirmation of free amine formation, Fmoc-Ile-OH (0.049 g, 0.14 mmol) was next coupled with tripeptide 35 without Fmoc functionality to give tetrapeptide 36. After the deprotection of NHFmoc functionality from 36 using 20% piperidine in DMF, finally N-Boc-His-OH (0.035 g, 0.14 mmol) was attached to the growing peptide chain to obtain pentapeptide 37. A mixture of 9.5 mL trifluoroacetic acid (TFA), 0.25 mL triisopropylsilane (TIPS), and 0.25 mL H$_2$O was prepared in a 15 mL centrifuge tube, and 5 mL of this cocktail solution was added to the resin beads, and nitrogen gas was bubbled through the solution for 30 minutes. The cocktail with cleaved Tub_06 in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved Tub_06 was transferred to a 15 mL centrifuge tube, fitted with a septum, and concentrated under reduced pressure to obtain a viscous liquid. Ice cold ether (5 mL) was added to the concentrated, viscous mixture to precipitate Tub_06 as a white solid, and the solid was washed thrice with ice-cold ether (5 mL×3). The product Tub_06 was purified by HPLC. The yield of the product was 25% yield. The molecular weight is determined by HRMS (+ESI) calcd for [M+H]$^+$ (C$_{26}$H$_{39}$N$_9$O$_7$S)$^+$: 622.2766 found 622.2771.

Figure 16:
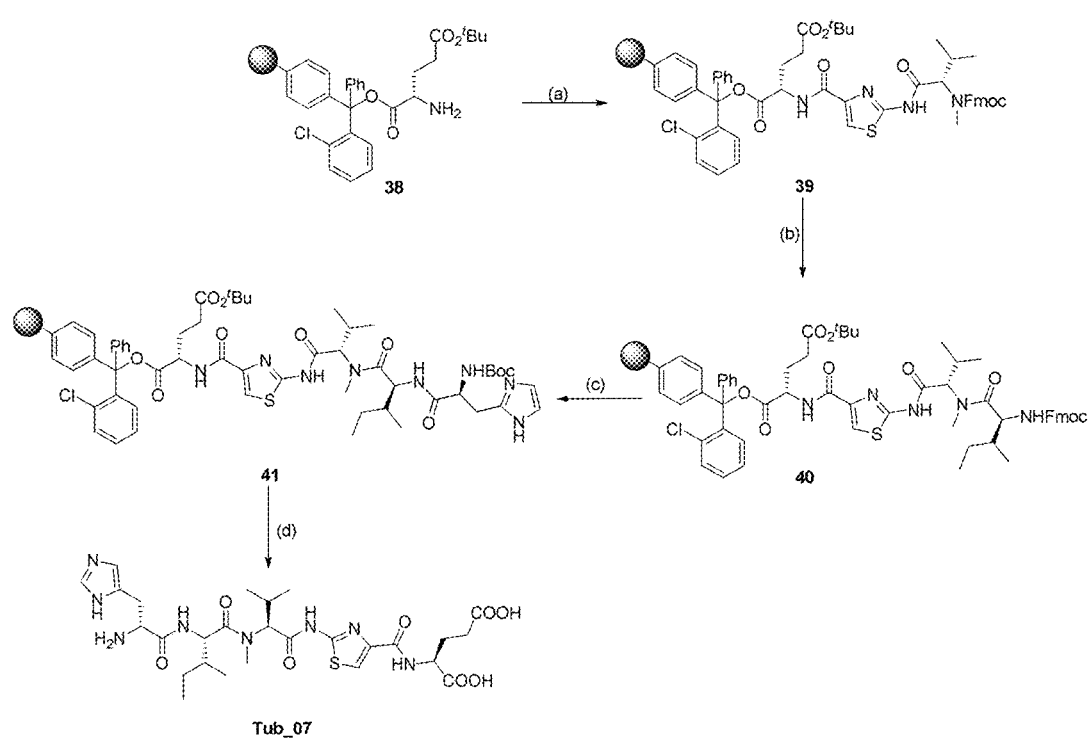
FIG. 16 illustrates a schematic representation of solid phase synthetic strategy for preparation of tubulysin derivative Tub_07, according to an embodiment as disclosed herein.

Preparation of Tub_07 (FIG. 16): In the first step, H-Glu (O$^t$Bu)-2-ClTrt resin 38 (0.1 g, 0.14 mmol) was swelled with dichloromethane (5 mL) by bubbling nitrogen for 30 minutes and then drain the solvent. Later the resin was further swelled with DMF (5 mL) thrice for 15 minutes each. Fmoc-NMe-Val-thiazole-OH 30b (0.072 g, 0.15 mmol), PyBOP (0.078 g, 0.15 mmol) and DIPEA (0.1 mL, 0.6 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads didn't show dark blue color, which suggest that the free amine groups of resin beads were coupled with 30b. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment 39. The resin beads were washed with DMF (3 mL×3), and isopropanol (3 mL×3), and the Kaiser test was performed. In the Kaiser test the beads turned to dark red in color indicating formation of free amino functionality in the tripeptide 39. After the confirmation of free amine formation, Fmoc-Ile-OH (0.053 g, 0.15 mmol) was next coupled with tripeptide 39 without Fmoc functionality to give tetrapeptide 40. After the deprotection of NHFmoc functionality using 20% piperidine in DMF, finally N-Boc-His-OH (0.038 g, 0.15 mmol) was attached to the growing peptide chain to obtain pentapeptide 41. A mixture of 9.5 mL trifluoroacetic acid (TFA), 0.25 mL triisopropylsilane (TIPS), and 0.25 mL $H_2O$ was prepared in a 15 mL centrifuge tube, and 5 mL of this cocktail solution was added to the resin beads, and nitrogen gas was bubbled through the solution for 30 minutes. The cocktail with cleaved Tub_07 in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved Tub_07 was transferred to a 15 mL centrifuge tube, fitted with a septum, and concentrated under reduced pressure to obtain a viscous liquid. Ice cold ether (5 mL) was added to the concentrated, viscous mixture to precipitate Tub_07 as a colorless solid, and the solid was washed thrice with ice-cold ether (5 mL×3). The product Tub_07 was purified by HPLC. The yield of the product was 18% yield. The molecular weight is determined by HRMS (+ESI) calcd for $[M+H]^+$ $(C_{27}H_{40}N_8O_8S)^+$: 637.2763 found 637.2759.

Figure 17:
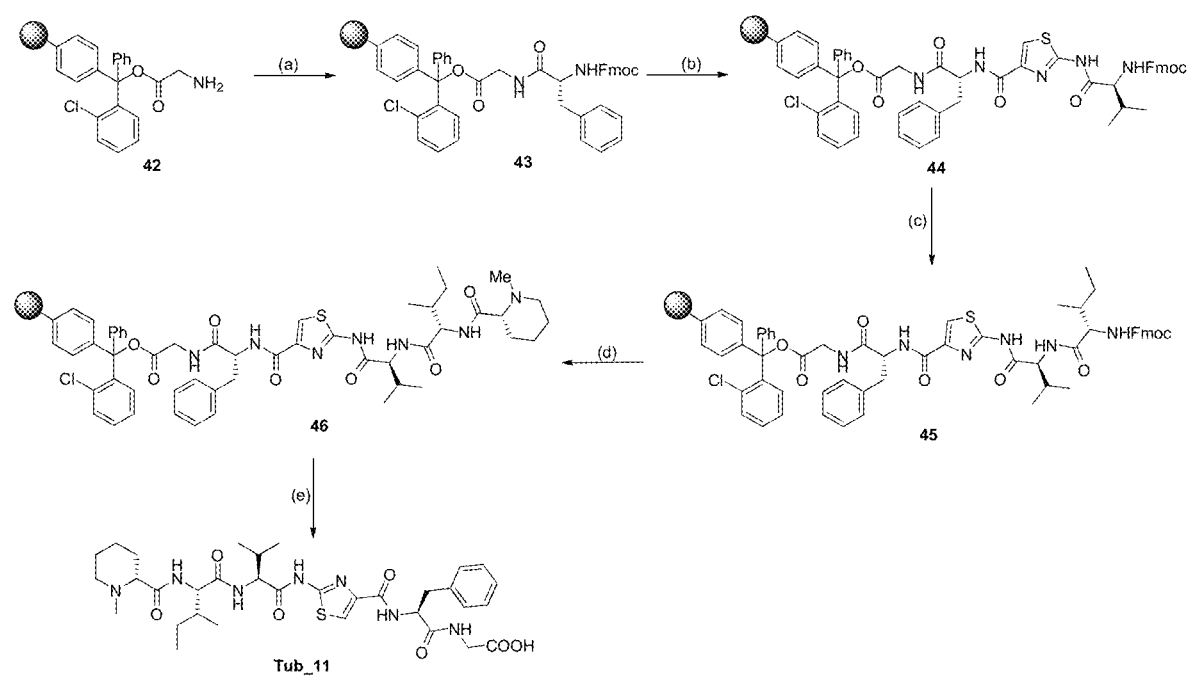
FIG. 17 illustrates a schematic representation of solid phase synthetic strategy for preparation of tubulysin derivative Tub_11, according to an embodiment as disclosed herein.

Preparation of Tub_11 (FIG. 17): In the first step, H-Gly-2-Chlorotrityl resin 42 (0.1 g, 0.04 mmol) was swelled with dichloromethane (5 mL) by bubbling nitrogen for 30 minutes and then drain the solvent. Later the resin was further swelled with DMF (5 mL×3) 15 minutes each. Fmoc-Phe-OH, (0.042 g, 0.11 mmol), PyBOP (0.057 g, 0.11 mmol) and DIPEA (0.07 mL, 0.44 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads were colorless, which suggest that the free amine groups of resin beads were coupled with 42. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment 42. The resin beads were washed with DMF (3 mL×3), and isopropanol (3 mL×3), and the Kaiser test was performed. The beads showed dark blue color, which suggest the formation of free amino functionality in the dipeptide 43. Fmoc-Val-thiazole-OH, 30 (0.051 g, 0.11 mmol), PyBOP (0.057 g, 0.11 mmol) and DIPEA (0.07 mL, 0.44 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads were colorless, which suggest that the free amine groups of resin beads were coupled with Fmoc-Val-thiazole-OH. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment Fmoc-Val-thiazole-OH. The resin beads were washed with DMF (3 mL×3), and isopropanol (3 mL×3), and the Kaiser test was performed. In the Kaiser test, the beads turned to dark red in color indicating formation of free amino functionality in the tetrapeptide 44. After the confirmation of free amin formation, Fmoc-Ile-OH (0.042 g, 0.11 mmol) was next coupled with 44 without Fmoc functionality to give pentapeptide 45. After the deprotection of NHFmoc functionality using 20% piperidine in DMF, finally N-methylpipecolic acid (0.015 g, 0.11 mmol) was coupled to the growing peptide chain to obtain hexapeptide 46. A mixture of 9.5 mL trifluoroacetic acid (TFA), 0.25 mL triisopropylsilane (TIPS), and 0.25 mL $H_2O$ was prepared in a 15 mL centrifuge tube, and 5 mL of this cocktail solution was added to the resin beads, and nitrogen gas was bubbled through the solution for 30 minutes. The cocktail with cleaved Tub_11 in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved Tub_11 was transferred to a 15 mL centrifuge tube, fitted with a septum, and concentrated under reduced pressure to obtain a viscous liquid. Ice cold ether (5 mL) was added to the concentrated, viscous mixture to precipitate Tub_11 as a white solid, and the solid was washed thrice with ice-cold ether (5 mL×3). The product Tub_11 was purified by HPLC. The yield of the product was 22% yield. The molecular weight is determined by HRMS (+ESI) calcd for $[M+H]^+$ $(C_{33}H_{47}N_7O_8S)^+$: 686.3330 found 686.3334.

Figure 18:
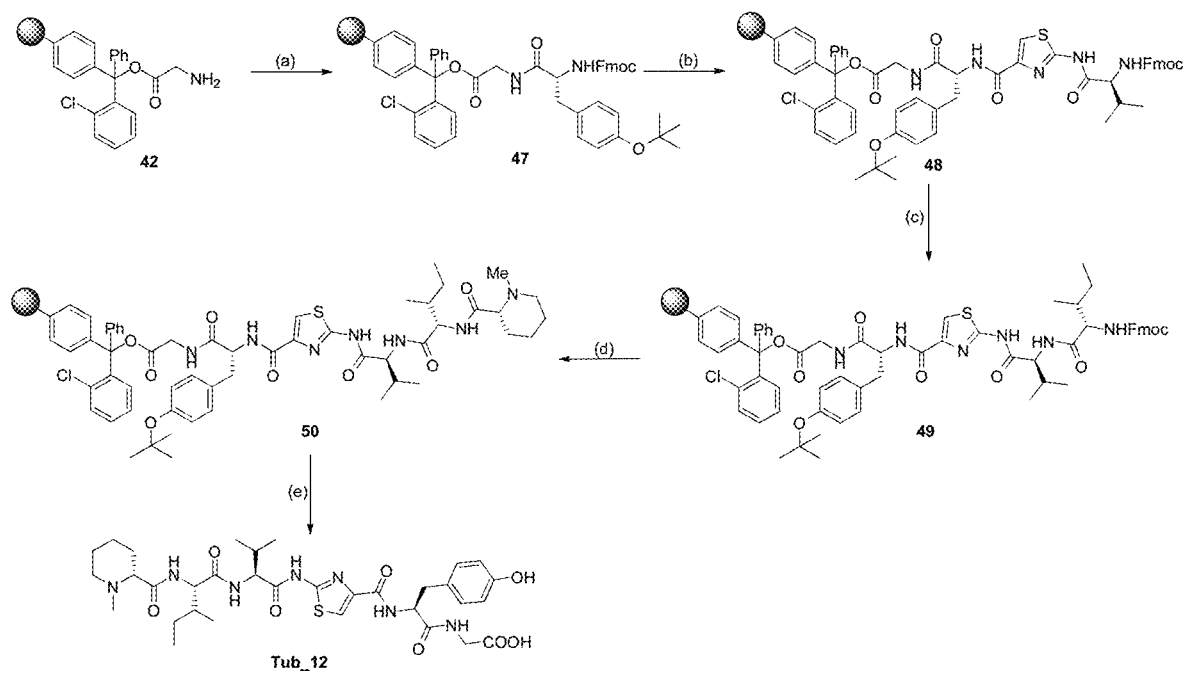
FIG. 18 illustrates a schematic representation of solid phase synthetic strategy for preparation of tubulysin derivative Tub_12, according to an embodiment as disclosed herein.

Preparation of Tub_12 (FIG. 18): In the first step, H-Gly-2-Chlorotrityl resin 42 (0.1 g, 0.04 mmol) was swelled with dichloromethane (5 mL) by bubbling nitrogen for 30 minutes and then drain the solvent. Later the resin was further swelled with DMF (5 mL×3) 15 minutes each. Fmoc-Tyr (tBu)—OH, (0.050 g, 0.11 mmol), PyBOP (0.057 g, 0.11 mmol) and DIPEA (0.07 mL, 0.44 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads were colorless, which suggest that the free amine groups of resin beads were coupled with 42. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment 47. The resin beads were washed with DMF (3 mL×3), and isopropanol (3 mL×3), and the Kaiser test was performed. The beads turned dark blue color, which suggest the formation of free amino functionality in the dipeptide 47. Fmoc-Val-thiazole-OH, 30 (0.051 g, 0.11 mmol), PyBOP (0.057 g, 0.11 mmol) and DIPEA (0.07 mL, 0.44 mmol) in DMF (1 mL) were added to the peptide vessel and the coupling reaction was continued for 6 h. The resin beads were washed with DMF (3 mL×3), followed by isopropanol (3 mL×3). The completion of the reaction was monitored by performing the Kaiser test. The beads were colorless, which suggest that the free amine groups of resin beads were coupled with Fmoc-Val-thiazole-OH. A solution of 20% piperidine in DMF (4 mL) was added to the peptide vessel, and the resin beads were bubbled for 10 minutes. The procedure was repeated twice (3 mL×2) to ensure the complete deprotection of the Fmoc protecting group from the coupled amino acid fragment Fmoc-Val-thiazole-OH. The resin beads were washed with DMF (3 mL×3), and isopropanol (3 mL×3), and the Kaiser test was performed. In the Kaiser test the beads turned to dark red in color indicating formation of free amino functionality in the tetrapeptide 48. After the confirmation of free amine formation, Fmoc-Ile-OH (0.038 g, 0.11 mmol) was next coupled with 7 without Fmoc functionality to give pentapeptide 49. After the deprotection of NHFmoc functionality using 20% piperidine in DMF, finally N-methylpipecolic acid (0.016 g, 0.11 mmol) was attached to the growing peptide chain to obtain hexapeptide 50. A mixture of 9.5 mL trifluoroacetic acid (TFA), 0.25 mL triisopropylsilane (TIPS), and 0.25 mL $H_2O$ was prepared in a 15 mL centrifuge tube, and 5 mL of this cocktail solution was added to the resin beads, and nitrogen gas was bubbled through the solution for 30 minutes. The cocktail with cleaved Tub_12 in peptide vessel was collected to a round bottom flask (25 mL). The resin beads were treated again with the cocktail solution twice (2.5 mL×2) for 15 minutes each, and the mother liquor was collected in the same round bottom flask (25 mL). The pooled cocktail mixture with cleaved Tub_12 was transferred to a 15 mL centrifuge tube, fitted with a septum, and concentrated under reduced pressure to obtain a viscous liquid. Ice cold ether (5 mL) was added to the concentrated, viscous mixture to precipitate Tub_12 as a white solid, and the solid was washed thrice with ice-cold ether (5 mL×3). Product Tub_12 was purified by HPLC. The yield of the product was 28% yield. The molecular weight is determined by HRMS (+ESI) calcd for $[M+H]^+$ $(C_{33}H_{47}N_7O_8S)^+$: 702.3280 found 702.3275.

In vitro studies against human cancer cell lines: After the in silico design and successful syntheses of the third generation tubulysin derivative, in vitro cytotoxicity assay was next performed. The tubulysin derivative, called Tub_01, was analyzed for its antitumor activity against various cancerous cell lines using crystal violet assay. Briefly, 4000 HeLa, MCF7, A549 and A431 cells/well were plated in a 96 well plate and incubated for 28 h and 48 h at 37° C. Tub_01 dilutions were prepared ranging from 1 pM to 100 µM for for HeLa, MCF7, A549 and A431 cell lines for an incubation period of 24 h. For an incubation period of 48 h, Tub_01 dilutions were prepared ranging from 1 pM to 100 µM, 1 nM to 200 µM and 10 pM to 100 µM for HeLa, MCF7, A549 and A431 cell lines respectively. The cytotoxicity of the Tub_01 was measured by crystal violet assay. The cells were washed with PBS buffer and incubated with 50 µL crystal violet dye. Followed by washing with buffer and air-dried overnight. 200 µL of methanol was added to each well and incubated for 20 min. The absorbance from each well proportional to the live cell was measured using Synergy H1 multimode plate reader (BioTek Instruments, Inc., Winooski, Vt., USA) at the wavelength of 520 nm.

Figure 19:
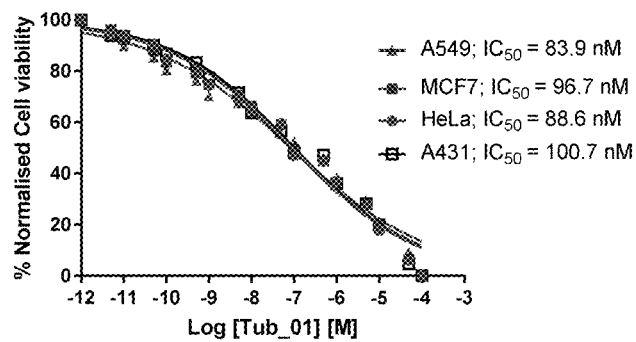
FIG. 19 illustrates $IC_{50}$ curve of tubulysin derivative Tub_01 in various cancerous cell lines for 24 h incubation, according to an embodiment as disclosed herein.
Figure 20:
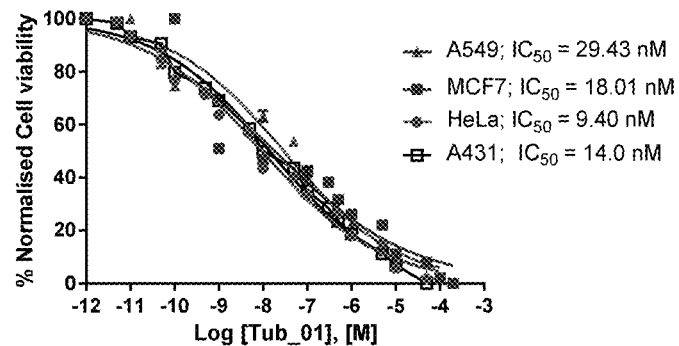
FIG. 20 illustrates $IC_{50}$ curve of tubulysin derivative Tub_01 in various cancerous cell lines for 48 h, according to an embodiment as disclosed herein.
Figure 21:
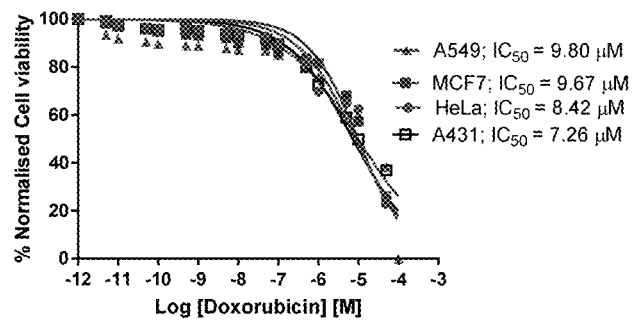
FIG. 21 illustrates $IC_{50}$ curve of standard anticancer drug, doxorubicin, in various cancerous cell lines for 24 h, according to an embodiment as disclosed herein.
Figure 22:
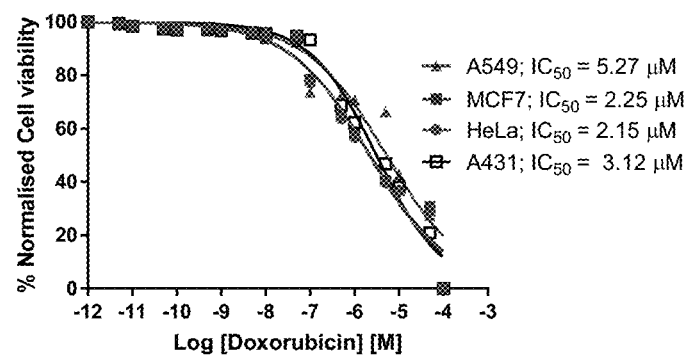
FIG. 22 illustrates $IC_{50}$ curve of standard anticancer drug, doxorubicin, in various cancerous cell lines for 48 h, according to an embodiment as disclosed herein.

Dose v/s response curves were obtained from a plot of log [Inhibitor] vs. normalized cell viability and $IC_{50}$ (concentration at which 50% of the tumor cells are killed by tubulysin derivative) was calculated for tubulysin derivative against tumor cells using GraphPad Prism, version 7.04 for Windows (GraphPad Software, San Diego, Calif.). For 24 h study, the half maximal inhibitory concentration ($IC_{50}$) of the inhibitor, tubulysin derivative was determined to be 83.9 nM, 96.7 nM, 88.6 nM and 100.7 nM for A549, MCF7, HeLa and A431 cells respectively (FIG. 19). For 48 h incubation studies, the half maximal inhibitory concentration ($IC_{50}$) of the tubulysin derivative was found to be 29.4 nM, 18.01 nM, 9.4 nM and 14 nM for A549, MCF7, HeLa and A431 cells respectively (FIG. 20). The potency or $IC_{50}$ of third-generation tubulysin derivatives were compared with standard anticancer drug, doxorubicin and the third-generation tubulysin derivatives were found to be 100-250-fold times more potent than doxorubicin (FIG. 21 and FIG. 22). From the in vitro assay, we have successfully demonstrated the cytotoxic potency of our novel tubulysin derivative Tub_01.

Embodiments also include pharmaceutical compositions comprising a therapeutic amount of compound of Formula I and Formula II.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. A compound of Formula I

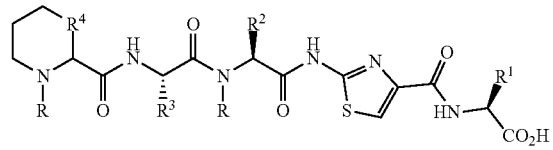

Formula I

Formula I
and its stereo isomers thereof, wherein R is a methyl group;

$R_1$ is one of $CH_2CONHTrt$, $(CH_2)_2COO^tBu$, and $CH_2COOH$•, $R_2$ is $CH(CH_3)_2$, $R_3$ is $CH(CH_3)CH_2CH_3$, and $R_4$ is -$(CH_2)_4$ or

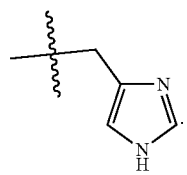 [SMILES: *Cc1c[nH]cn1]

2. A compound of Formula II

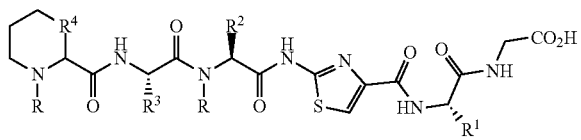

Formula II

Formula II
and its stereoisomers thereof, wherein R is a methyl or hydrogen group;
R$_1$ is one of CH$_2$COO$^t$Bu, (CH$_2$)$_2$COO$^t$Bu, CH$_2$Ph, and CH$_2$—C$_6$H$_4$-p-O$^t$Bu•, R$_2$ is CH(CH$_3$)$_2$, R$_3$ is CH(CH$_3$) CH$_2$CH$_3$, and
R$_4$ is-(CH$_2$)$_4$ or

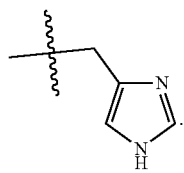

3. A process for preparation of compound of Formula I as claimed in claim 1, the process comprising:
a) obtaining an intermediate of the following formula:

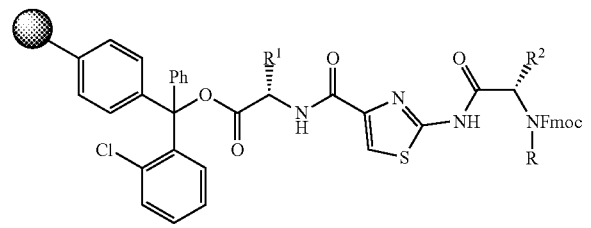

wherein R is H or Me, R$_1$ is one of CH$_2$CONHTrt, (CH$_2$)$_2$COO$^t$Bu, and CH$_2$COOH•, R$_2$ is CH(CH$_3$)$_2$
b) exposing a deprotection reagent to the intermediate to remove the Fmoc protecting group from the intermediate to obtain an activated amino acid; and
c) reacting the activated amino acid with Fmoc-Ile-OH followed by Nmethylpipecolic acid or Boc-His-OH in a sequential manner to obtain the compound of formula I.
4. The process as claimed in claim 3, wherein the intermediate is obtained by contacting an activated resin selected from a group consisting of H$^{L\text{-}Asn(Trt)\text{-}2CT}$ resin or H-L-Glu (OtBu)-2-ClTrt resin or H-L$^{Asp(OtBu)\text{-}2ClTrt}$resin with Fmoc-NH-Va1-thiU01e-OH or FmocNMe-valine-thiazole in the presence of a coupling agent to obtain the intermediate.
5. The process as claimed in claim 3, wherein the ratio of the resin to the amino acid (Fmoc-NH-Val-thiazole-OH or Fmoc-NMe-valine-thiazole) is in the range of 1:2 to 1:3.
6. The process as claimed in claim 3, wherein the deprotecting agent is a solution of 20% piperidine in DMF.
7. A process for preparation of compound of Formula II as claimed in claim 2, the process comprising:
a) obtaining an intermediate of the following formula:

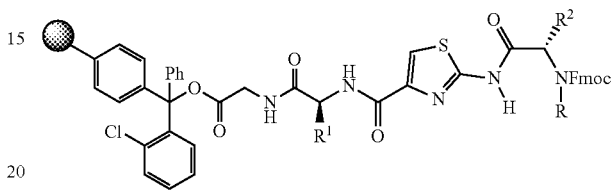

wherein R is a methyl group; R$_1$ is one of CH$_2$COO$^t$Bu, (CH$_2$)$_2$COO$^t$Bu, CH$_2$Ph, and CH$_2$—C$_6$H$_4$-p-O$^t$Bu; and R$_2$ is CH(C$_3$)$_2$,
d) exposing a deprotection reagent to the intermediate to remove the Fmoc protecting group from the intermediate to obtain an activated amino acid; and
e) reacting the activated amino acid with Fmoc-Ile-OH followed by Nmethylpipecolic acid or Boc-His-OH in a sequential manner to obtain the compound of formula II.
8. The process as claimed in claim 7, wherein the intermediate is obtained by contacting an activated resin (H-Gly-2-Chlorotrityl resin) with a Fmoc-Glu(γ-O$^t$Bu)—OH or Fmoc-Asp(O$^t$Bu)—OH or Fmoc-Phe-OH or Fmoc-Tyr ($^t$Bu)—OH in the presence of a coupling agent to obtain the intermediate.
9. The process as claimed in claim 8, wherein the ratio of the resin to the amino acid (Fmoc-Glu(y-O$^t$Bu)—OH or Fmoc-Asp(O$^t$Bu)—OH or Fmocme-OH or Fmoc-Tyr ($^t$Bu)—OH) is in the range or 1:2.5 to 1:3.5.
10. The compound of Formula I as claimed in claim 1 include

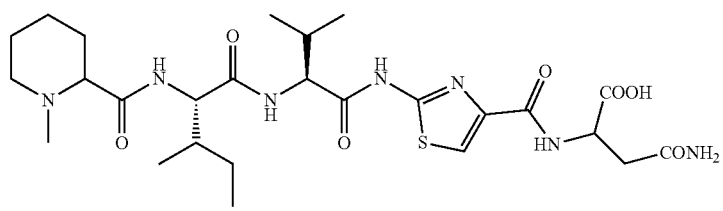

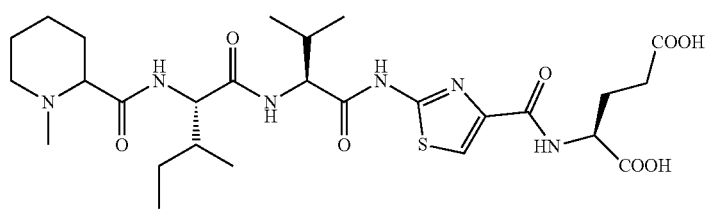

Tub_02

-continued
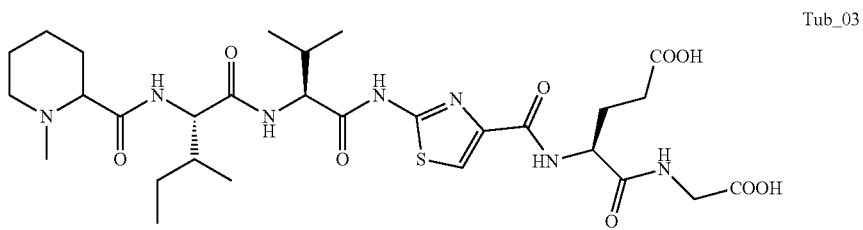
Tub_03
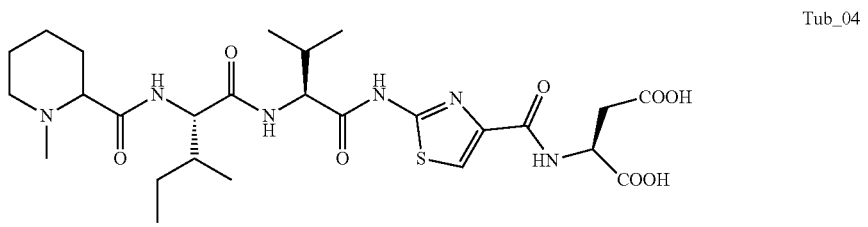
Tub_04
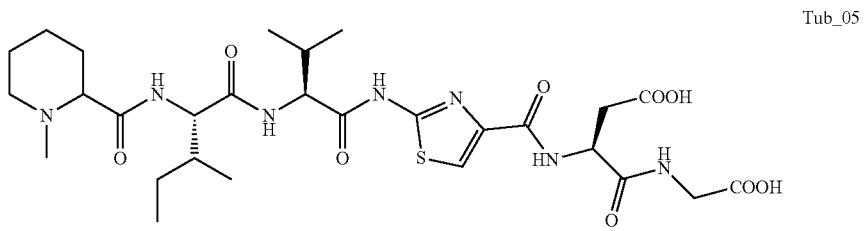
Tub_05
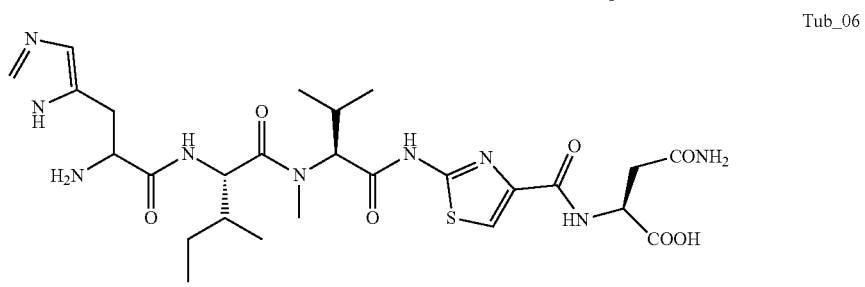
Tub_06
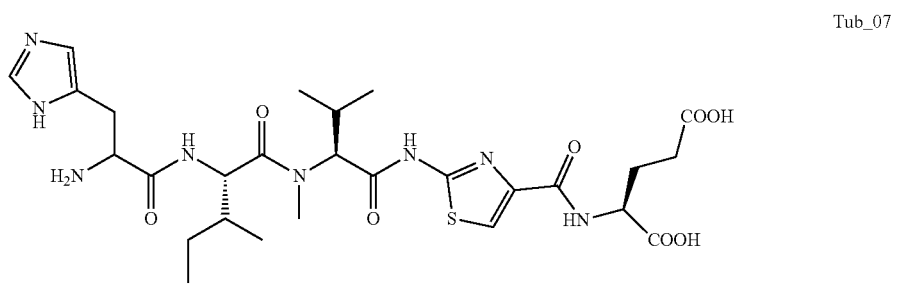
Tub_07
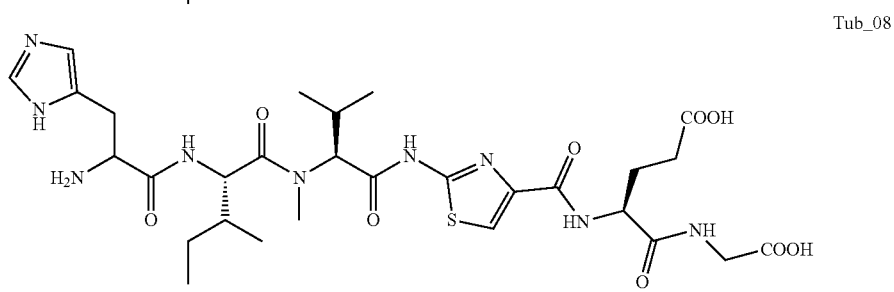
Tub_08

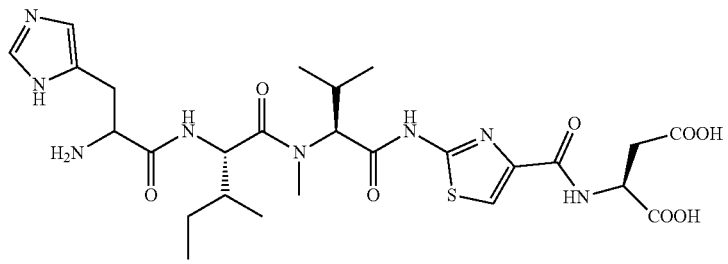
Tub_09
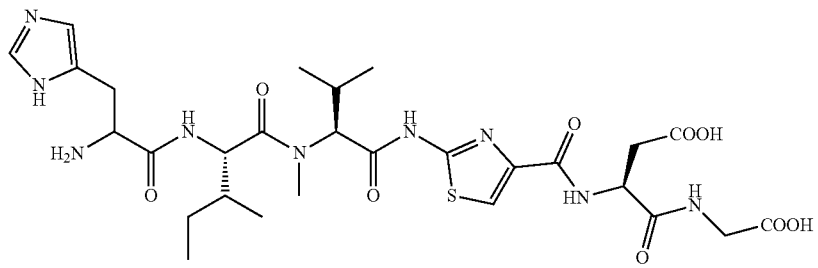
Tub_10
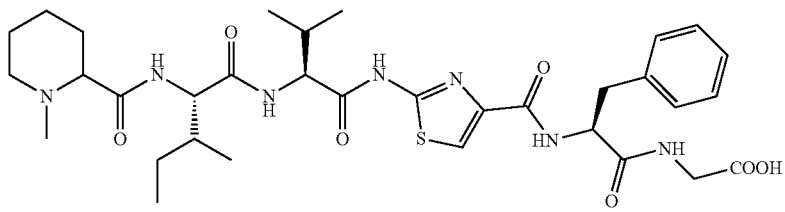
Tub_11
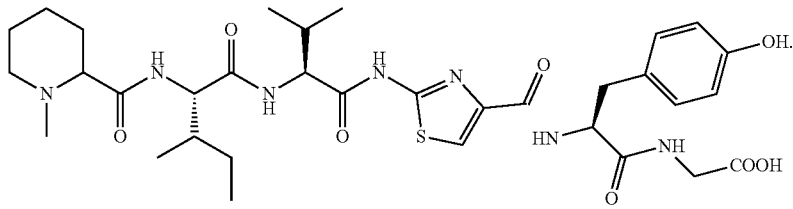
Tub_12
11. A pharmaceutical composition comprising a therapeutic amount of compound of Formula I or Formula II.
12. The compound of Formula II as claimed in claim 2 include
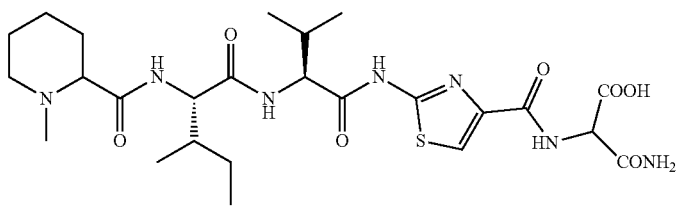
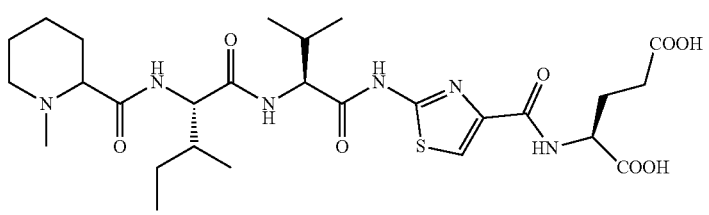
Tub_02

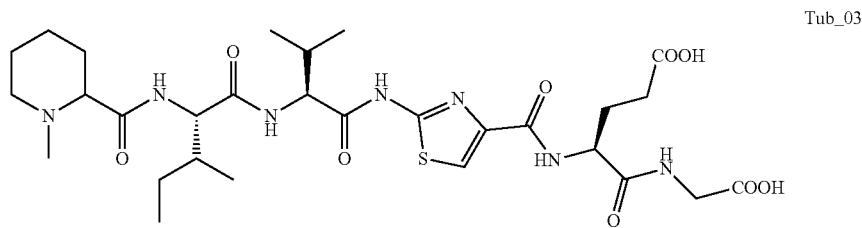
Tub_03
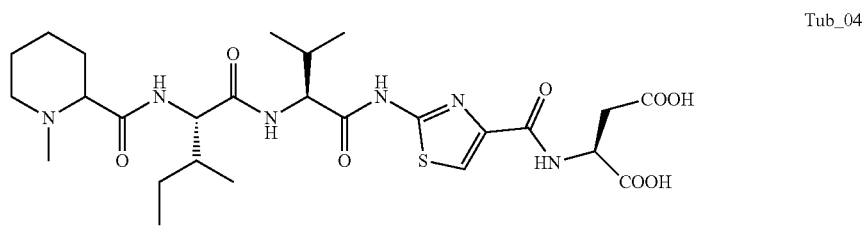
Tub_04
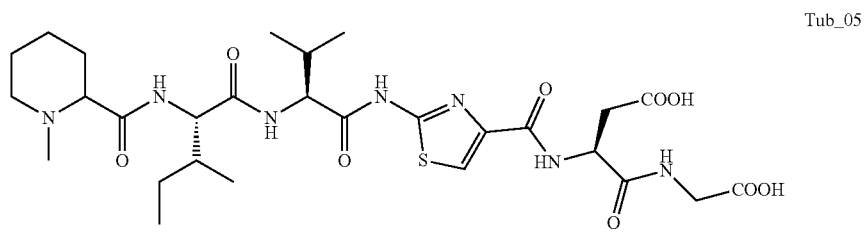
Tub_05
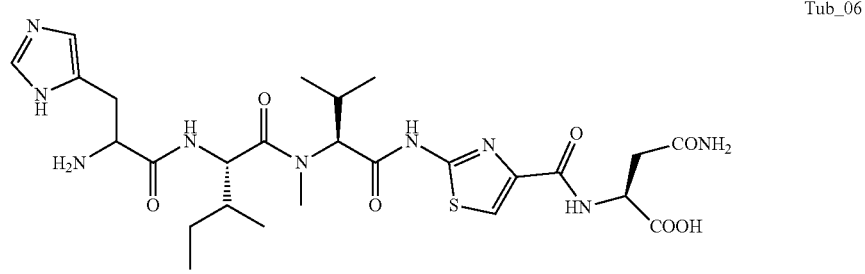
Tub_06
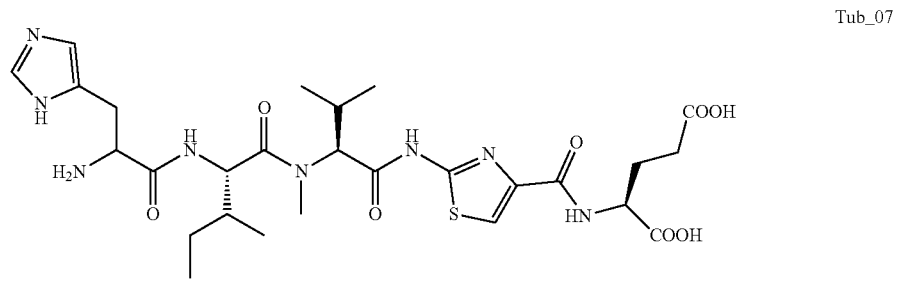
Tub_07
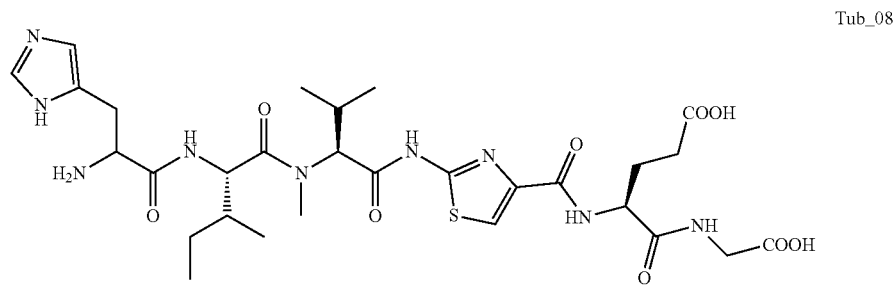
Tub_08

-continued
Tub_09
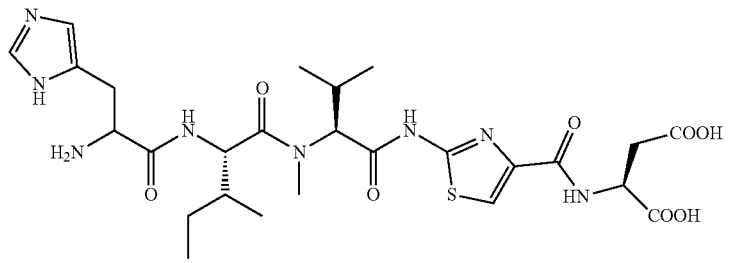
Tub_10
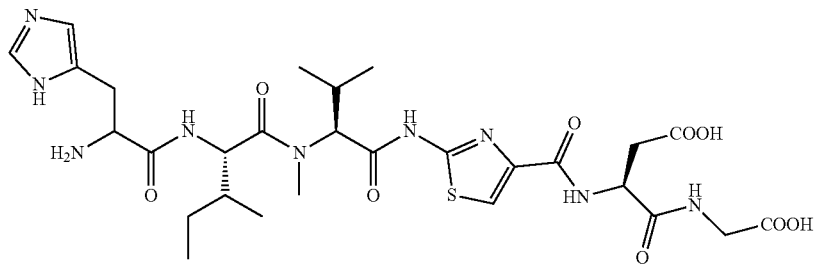
Tub_11
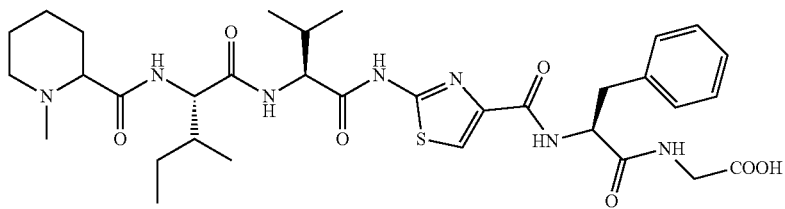
Tub_12
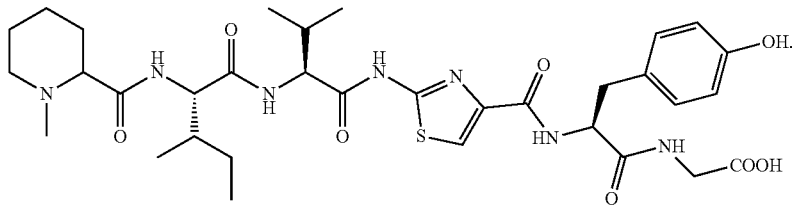
* * * * *